United States Patent [19]
Marx

[11] Patent Number: 5,631,019
[45] Date of Patent: May 20, 1997

[54] BIOLOGIC BIOADHESIVE COMPOSITIONS CONTAINING FIBRIN GLUE AND LIPOSOMES, METHODS OF PREPARATION AND USE

[75] Inventor: Gerard Marx, New York, N.Y.

[73] Assignee: New York Blood Center, Inc., New York, N.Y.

[21] Appl. No.: 460,534

[22] Filed: Jun. 2, 1995

Related U.S. Application Data

[62] Division of Ser. No. 198,158, Feb. 17, 1994, abandoned.

[51] Int. Cl.$^6$ ..................................................... A61K 9/127
[52] U.S. Cl. ........................ 424/450; 424/422; 424/424; 424/426; 424/484
[58] Field of Search ................................. 424/450, 484, 424/422, 424, 426

[56] References Cited

U.S. PATENT DOCUMENTS

| | | | |
|---|---|---|---|
| 4,224,179 | 9/1980 | Schneider | 264/46 |
| 4,235,871 | 11/1980 | Papahadjopoulos et al. | 424/450 |
| 4,351,337 | 9/1982 | Sidman | 128/260 |
| 4,708,861 | 11/1987 | Popmacu et al. | 424/11 |
| 4,853,225 | 8/1989 | Wahlig | 424/423 |
| 5,206,023 | 4/1993 | Hunziker | 424/423 |
| 5,209,776 | 5/1993 | Bass et al. | 106/124 |
| 5,246,452 | 9/1993 | Sinnott | 623/1 |
| 5,290,552 | 3/1994 | Sievva | 424/94.64 |

FOREIGN PATENT DOCUMENTS

| | | |
|---|---|---|
| 0160266 | 11/1985 | European Pat. Off. . |
| WO8503640 | 8/1985 | WIPO . |

OTHER PUBLICATIONS

C. Pidgeon and C.A. Hunt, 1987, "Photolabile liposomes as Carriers", *Meths. Enzymol.*, 149(13):99–111.

S. Perrell et al., 1991, "A Simple Method for the Preparation of Liposomes for Pharmaceutical Applications: Characterization of the Liposomes", *J. Pharm. Pharmacol.*, 43:154–161.

S.S. Davis and I.M. Walker, 1987, "Multiple Emulsions as Targetable Delivery Systems", *Meths. Enzymol.*, 149:51–87.

F. Szoks, Jr. and D. Paphadjopoulos, 1980, "Comparative Properties and Methods of Preparation of Lipid Vasicles (Liposomes)", *Ann. Rev. Biophys. Bioeng.*, 9:467–508.

V.P. Torchilin et al., 1978, "Comparative Studies on Covalent and Noncovalent Immobilization of Protein Molecules on the Surface of Liposomes", *Biochem. Biophy. Res. Commun.*, 85 (3):983–990.

(List continued on next page.)

*Primary Examiner*—Gollamudi S. Kishore

[57] ABSTRACT

The present invention describes a biologically compatible bioadhesive sealant composition comprising fibrin glue and liposomes for use in mammals, including humans. Fibrin glue of the invention comprises fibrinogen and thrombin which are mixed together in various modes with liposomes and applied to a site of injury, to a wound, or to a surgical or nonsurgical incision or opening. In accordance with the invention, the liposomes are embedded within the fibrin glue after coagulation has occurred, and may release bioactive substances contained within their aqueous interiors to promote healing and protection during the recovery process. The bioadhesive composition of the invention promises to maintain hemostasis after surgeries and improves upon existing glues or gel formulations due to its complete biological compatibility, its formation in situ, and its provision of bioactive therapeutics via entrapped liposomes directly to the site. Long-lasting biophysical and biomechanical properties as well as therapeutic value are imparted to the fibrin glue components by the liposome component of the composition. The biocompatible fibrin glue and liposome composition is also amenable for fabrication into films, coatings, or membranes for in vitro and in vivo uses.

34 Claims, 12 Drawing Sheets

OTHER PUBLICATIONS

G. Firth, 1984, "Studies on the Intracerebral Injection of Bleomycin Free and Entrapped Within Liposomes in the Rat", *J. Neurol. Neurosurg. Psychiat.*, 47:585–589.

G. Poste, 1980, "The Interaction of Lipid Vesicles (Liposomes) with Cultured Cells and their use as Carriers for Drugs and Macromolecules", In: *Liposomes in Biological Systems*, Eds. G. Gregoriadis and A.C. Allison, John Wiley and Sons, Ltd., pp. 101–151.

D. Goren et al., 1990, "The Influence of Physical Charscleristics of Liposomes Containing Doxorubicin on their Pharmacological Behavior", *Biochem. Biophys. Acta.*, 1029:285–294.

BIOLOGIC BIOADHESIVE COMPOSITIONS CONTAINING FIBRIN GLUE AND LIPOSOMES, METHODS OF PREPARATION AND USE

This is a divisional of application U.S. Ser. No. 08/198, 158 filed on Feb. 17, 1994, now abandoned.

FIELD OF THE INVENTION

The invention describes bioadhesive sealant compositions containing fibrin glue comprising human-source components in combination or admixture with liposomes, and methods for making the compositions. Compositions and methods of the invention are suitable for accelerating and ameliorating the healing process after various types of surgical and nonsurgical procedures or wound healing in mammals, including humans, and for maintaining hemostasis.

BACKGROUND OF THE INVENTION

Bioadhesive Fibrin Glue

Increased experience has been gained in the use of fibrin glue among various surgical disciplines (Lerner, R. and Binur, N. S., 1990, *J. Surg. Res.*, 48: 165–181; Gibble, J. W. and Ness, P. M., 1990, *Transfusion*, 30:741–747; Sierra, D. H., 1993, *J. Biometer. Applic.* 7, 309–352; Brennan, M., 1991, *Blood Reviews.*, 5:240–244; Dresdale A., et al., 1985, *Surgery*, 97:750–755; Sponitz W., et al., 1987, *Amer. Surg.*, 59:460–462; Schlag G. and Redl H (Eds), 1986, *Gynecology and Obstetrics-Urology*. Fibrin Sealant in Operative Medicine, Vol 3, Springer Verlag (Berlin); Burnouf-Radosevich, M. et al., 1990, *Vox Sang*, 58:77–84). For example, surgeons, dentists and hematologists have reported that fibrin glue is an effective bioadhesive. Experience in animals and humans suggests that an advantage of using fibrin glue rather than synthetic plastics (e.g., cyanoacrylate) or sutures is that fibrin glue promotes local coagulation, thereby preventing bleeding even in hemophiliacs. Fibrin glue also appears to support regrowth of new tissue and the extracellular matrix.

Fibrin glue is formed by mixing two components, human fibrinogen (or a source of fibrinogen, such as a freeze-dried plasma protein concentrate of fibrinogen/factor XIII/fibronectin) and an activating enzyme such as thrombin. Prior to use, the plasma protein concentrates are conventionally solubilized in the presence of calcium chloride. Thrombin-induced activation of fibrinogen results in the formation of fibrin. Factor XIII and calcium participate in the cross-linking and stabilization of fibrin to become a tight mesh of polymeric fibrin glue. Applied to tissue, the fibrin clot adheres to the site of application. The rate of coagulation and mechanical properties of the clot are dependent on the concentration of fibrinogen as well as thrombin. Traditional fibrin glue preparations are described in International Application No. WO93/05067 to Baxter International, Inc.; WO92/13495 to Fibratek, Inc.; and WO91/09641 to Cryolife, Inc.

Thrombin is a common physiological instigator of clotting. Thrombin from a number of mammalian sources, most commonly bovine, is routinely used in commercially-available fibrin glues. Human thrombin can be employed in the formulation of the liposome-containing fibrin glue bioadhesive, as can other appropriate catalyzing enzymes, such as reptilase or select venoms (Fenton II, J. W. et al., 1977, *J. Biol. Chem.*, 252:3587–3598; Gaffney P. J. et al., 1992, *Thrombos. Haemostas.*, 67:424–427; European Patent Application No. EP 0 439 156 A1, 1991; Stocker K., et al., 1982, *Toxicon.*, 20:265–273; Pirkle H. and Stocker K., 1991, *Thrombos. Haemostas.*, 65:444–450).

Fibrinogen may be in an intimate admixture with other proteins that are typically found in uncoagulated whole blood, in platelet-rich plasma, in plasma, in cryoprecipitate, or in precipitates of plasma obtained by a method such as Cohn precipitation of plasma. Such additional protein components may include fibronectin, immunoglobulin, particularly IgG, factor XIII, plasminogen, and albumin.

The fibrinogen preparations used in the fibrin glue and liposome compositions can be virally inactivated by one or more methods prior to their employment in the invention (e.g. Examples 1–3).

Both fibrinogen and thrombin are derived from blood plasma by the fractionation of plasma. Comprehensive reviews on the preparative techniques of each have been published and are the basis for most commercial plasma fractionation procedures used by those skilled in the art and suitable for use in the invention (For fibrinogen: Blomback, B. and Blomback, M., 1956, *Ark Kemi*, 10:415–443; Stryker, M. H. & Waldman, A. A., 1978, *Kirk-Othmer Encyclopedia of Chemical Technology*, Vol 4, 3rd ed., pp 25–61, John Wiley; Lowe G. D. O. et al., 1987, Fibrinogen 2: Biochemistry, Physiology and Clinical Relevance. Excerpta Medicus, Elsevier Science Publishers; For thrombin: Fenton II, J. W. et al., 1977, *J. Biol. Chem.*, 252:3587–3598; Gaffney P. J. et al., 1992, *Thrombos. Haemostas.*, 67:424–427; Ward, G., 1991, European Patent Application No. EP 0 439 156 A1; and U.S. Pat. No. 5,143,838 to Kraus et al.).

Alternative sources of human fibrinogen are also envisioned. For example, fibrinogen made by recombinant techniques could also be employed in the fibrin glue and liposome composition. Molecular techniques available for the production of recombinant fibrinogen include the use of COS-1 or Hep G2 cells transfected with DNA vectors containing isolated genes encoding normal or mutant human fibrinogen (Roy S. N. et al., 1991, *J. Biol. Chem.*, 266:4758–4763; Roy S. N. et al., 1994, *J. Biol. Chem.*, 269:691–695). It is expected that future developments will lead to the ability to produce usable amounts of fibrinogen by such techniques in other types of cells. Normal or mutant recombinant fibrinogens may be employed in fibrin glue compositions formulated with the types of liposomes as described herein.

Despite the effectiveness and successful use of fibrin glue by medical practitioners in Europe, neither fibrin glue nor its essential component fibrinogen is widely used in the United States at the present time because of the general risks and problems of infection from pooled blood products contaminated with lipid-enveloped viruses such as HIV, associated with AIDS, and the hepatitis-causing viruses such as HBV and HCV (also known as non A-non B hepatitis virus), as well as cytomegalovirus (CMV), Epstein-Barr virus, and the herpes simplex viruses in fibrinogen preparations. For similar reasons, human thrombin is not currently authorized for human use in the United States. Bovine thrombin, which is licensed for human use in the United States, is obtained from bovine sources which do not appear to carry significant risks for HIV and hepatitis, although other bovine pathogens may be present.

Both human fibrinogen and human thrombin can be virally inactivated against lipid coat viruses by treatment with organic solvent and detergent (SD process) (U.S. Pat.

No. 4,540,573 to Neurath A. R. and Horowitz B., 1985; Horowitz, B. et al., 1985, *Transfusion*, 25:516–522; Horowitz, B. et al., 1992, *Blood*, 79:826–831; Piet, M. P. J. et al., 1990, *Transfusion.*, 30:591–598; Burnouf-Radosevich et al., 1990, *Vox Sang*, 58:77–84; Horowitz, B. et al., 1992, *Blood*, 79:826–831). Other viral inactivation procedures for fibrinogen and thrombin blood products include UV irradiation or heating (U.S. Pat. No. 5,116,590 to Miyano, K. et al.).

Liposomes

Liposomes are unilamellar or multilamellar lipid vesicles which entrap a significant fraction of aqueous solution. The vesicular microreservoirs of liposomes can contain a variety of water-soluble materials, which are thus suspended within the emulsion (reviewed in G. Gregorius (Ed.), 1991, *Liposome Technology*, Vols. I, II, III, CRC Press, Boca Raton, Fla.; M. J. Ostro (Ed.), 1983, *Liposome Preparations: Methods & Mechanisms*, Marcel Dekker Inc. New York; Davis S. S. and Walker I. M., 1987, *Methods in Enzymology*, 149:51–64; Mayhew E. et al., 1987, *Methods in Enzymology.*, 149:64–77; Shafer-Korting M. et al., 1989, *J. Am. Acad. Dermatol.*, 21:1271–1275; Szoka F. and Papahadjiopoulos D., 1980, *Ann. Rev. Biophys. Bioengin.*, 9:467–508; Harrigan P. R. et al., 1990, *Chem. & Phys. Lipids*, 52:139–149; Patel H. M., 1985, *Trans. Biochem. Soc.*, 13:513–516; Ostro M. J., 1987 (Jan.), *Sci. Am.*, 91). The preparation of liposomes and the variety of uses of liposomes in biological systems have been disclosed in U.S. Pat. No. 4,708,861 to M. C. Popescu et al., U.S. Pat. No. 4,224,179 to M. Schneider, U.S. Pat. No. 4,235,871 to D. P. Papahadjopoulos and F. C. Szoka, Jr., P. R. Cullis et al., 1987, In: *Liposomes as Pharmaceuticals*, M. J. Ostro, Ed., Marcel Dekker, New York, 39–72, and H. G. Weder et al., 1986, In: *Liposomes as drug carriers*, K. H. Schmidt, Ed., Thieme, Stuttgart, 26–39.

Liposomes are formed by mixing long chain carboxylic acids, amines, and cholesterol, as well as phospholipids, in aqueous buffers. The organic components spontaneously form multilamellar bilayer structures (i.e. liposomes). Depending on their composition and storage conditions, liposomes exhibit varying stabilities. Liposomes serve as models of cell membranes and also have been used as drug delivery systems (M. Schafer-Korting et al., 1989, *J. Am. Acad. Dermatol.*, 21:1271–1275). Most attempts to use liposomes as drug delivery vehicles have envisioned liposomes as entities which circulate in blood, to be taken up by certain cells or tissues in which their degradation would slowly release their internal aqueous drug-containing contents. In an effort to aid in their up-take by a given target tissue, some liposomes have been "tailored" by binding specific antibodies or antigens to the outer surface. Liposomes have also been devised as controlled release systems for delivery of their contents in vivo (H. M. Patel, 1985, *Biochem. Soc. Transactions*, 13:513–516). Compositions in which liposomes containing biologically active agents are maintained and immobilized in polymer matrices, such as methycellulose, collagen, and agarose, for sustained release of the liposome contents, are described in U.S. Pat. No. 4,708,861 to M. C. Popescu et al.

Fibrin Glue

Fibrin glue has the potential to be prepared in virally sterilized form by treating the fibrinogen and thrombin by viral inactivation processes, such as the solvent-detergent or SD process. There is ample opportunity to improve fibrin glue, fibrin glue compositions, and the utility of fibrin glue in wound healing. Various strategies have been used in attempts to improve the effectiveness of existing and commercially available fibrin glues by adding water soluble components to the fibrin glue preparation. Selective additives such as antibiotics (e.g. tobramycin or sisomicin), growth factors (e.g. EGF, TGF-$\beta$), peptides, proteins, fatty acid derivatives, vitamins, hormones, steroids, and trace elements (e.g. calcium phosphate) have been included directly in the fibrin glue formulation in an effort to influence cell growth and wound healing, and to prevent infection. However, because the extraneous additives were supplied directly in the fibrin glue or in an adhesive, the half-life of the additive may be affected. Direct addition of additives to fibrin glue may not be optimal for delayed, controlled, or long-term release of an agent.

Other difficulties encountered by mixing extraneous additives directly into fibrin glue components occur because the added materials may affect the rate of gelation or the mechanical properties of the fully-formed fibrin glue. Additives such as peptides may become cross-linked to the glue, and thus not be biologically available or effective in cross-linked form. Some additives might alter the enzymatic or biologic properties of thrombin. Alternatively, the additives might increase the susceptibility of the fibrin glue matrix to plasmin-induced degradation. Further, some additives might simply diffuse out of the fibrin matrix too rapidly, thereby decreasing the "window" of their pharmacologic effectiveness. Such problems bespeak the need for different techniques for combining fibrin glue with exogenously-added substances.

The present invention affords a new generation of virally inactivated bioadhesive sealant compositions comprising fibrin glue and liposomes whose advantages and uses will become apparent from the following objectives of the invention and disclosure. The present invention establishes a safe and unique fibrin glue and liposome formulation for widespread use and numerous surgical and nonsurgical applications.

Further, topical therapies call for a need for drug delivery systems in order to more effectively deliver active ingredients to the site of disease. The present invention provides a solution for several problems in the realm of drug delivery and improves upon extant methods. The present invention provides a wholly biologically compatible bioadhesive system while concurrently providing efficient and sustained delivery of therapeutic agents directly at and around the required site of administration.

SUMMARY OF THE INVENTION

It is an object of the present invention to provide a biological composition in which fibrin glue and liposomes are combined together to form a distinctive and novel bioadhesive for administration to animals, including humans. The final fibrin glue and liposome bioadhesive formulation may be achieved in a number of different ways, such as by premixing at least one of the fibrin glue components with liposomes prior to application or administration, and then adding the remaining component(s) to form in situ the final liposome-containing fibrin glue.

It is another object of the invention to provide liposomes tailored for use in conjunction with fibrin glue in various modes. In one mode, a fibrinogen solution can be mixed with liposomes and stored in the cold (i.e., at 4° C.), or frozen (i.e., at −30° C.), or lyophilized. When desired, the fibrinogen/liposome mixture is thawed or reconstituted with buffer, and then mixed with thrombin at the site of a surgical or non-surgical opening or wound, thereby forming liposome-containing fibrin glue. Alternatively, liposomes can be pre-mixed with a solution of thrombin and stored cold, frozen, or lyophilized. When desired, thawed, warmed, or reconstituted fibrinogen is mixed with a thrombin and liposome mixture at the site of administration, thereby forming liposome-containing fibrin glue.

It is a further object of the invention to provide a stable fibrin glue and liposome sealing matrix which is inexpensive and safe and can be easily applied over a surgical or nonsurgical wound or opening, or injury site, or a graft site in a mammal, including humans, to promote, accelerate, and protect sealing and healing at and around the site. The fibrin glue and liposome formulation remains at the site of application long enough to promote and protect the healing process. The fibrin glue is generally metabolized during wound healing and does not trigger an adverse reaction, toxicity, or an immune response in the recipient animal.

It is another object of the invention to provide a fibrin glue-containing liposome composition in which medicaments or bioactive additives are encapsulated or entrapped in the liposomes. The liposomes serve as vehicles or carriers of the medicaments and additives at an injury site, surgical or nonsurgical opening, or wound. The contents of the liposomes are released at the site after application, either in a spontaneous or controlled fashion.

Another object of the invention is to provide a novel method for formulating fibrin glues to improve upon existing methods for better protection and treatment of surface wounds and surgical and nonsurgical openings.

Yet another object of the invention is to provide fibrin glue and liposome bioadhesive compositions in which the liposomes add desirable properties to the glue components. The storage characteristics of both thrombin and fibrinogen may be modulated and significantly improved by liposome components. Biophysical properties of the fibrin glue composition, such as rate of gelation, viscoelasticity, and tensile strength, may be modulated and further improved by the liposome components of the composition.

A further object of the invention is to provide fibrin glue as the basis for clot formation at the site of injury, surgery, or a wound while simultaneously providing the slow or rapid release of bioactive ingredients which are contained in the liposomes of the fibrin glue/liposome formulation. The formulation may comprise a number of different types of liposomes, each containing a different bioactive agent. Alternatively, the formulation may comprise a number of liposomes of a particular type, each containing different additives.

Another object of the invention is to provide a biologically compatible sealing agent comprising fibrin glue combined with liposomes to favor and maintain hemostasis following its use, even in heparinized individuals and in individuals suffering from coagulopathies. In addition, the fibrin glue and liposome-containing bioadhesive system of the invention promises to reduce the incidence of fistula formation and to decrease postoperative infections, tissue necrosis, and toxicity.

Yet another objective of the invention is to provide fibrin glue compositions containing virally inactivated fibrinogen and thrombin preparations admixed with liposomes and other glue components from human and animal sources to yield a virally inactivated fibrin glue and liposome preparation. Such virally inactivated fibrin glue and liposome compositions afford safer and contaminant-free preparations which can be admixed and employed in accordance with the invention.

BRIEF DESCRIPTION OF THE DRAWINGS

FIG. 10. Photograph of fibrin glue (45 mg/mL fibrinogen) containing Type A liposomes (8% by volume) formulated into a film. The strip of fibrin glue and liposome film is being twisted 90°.

DETAILED DESCRIPTION OF THE INVENTION

Figure 1:
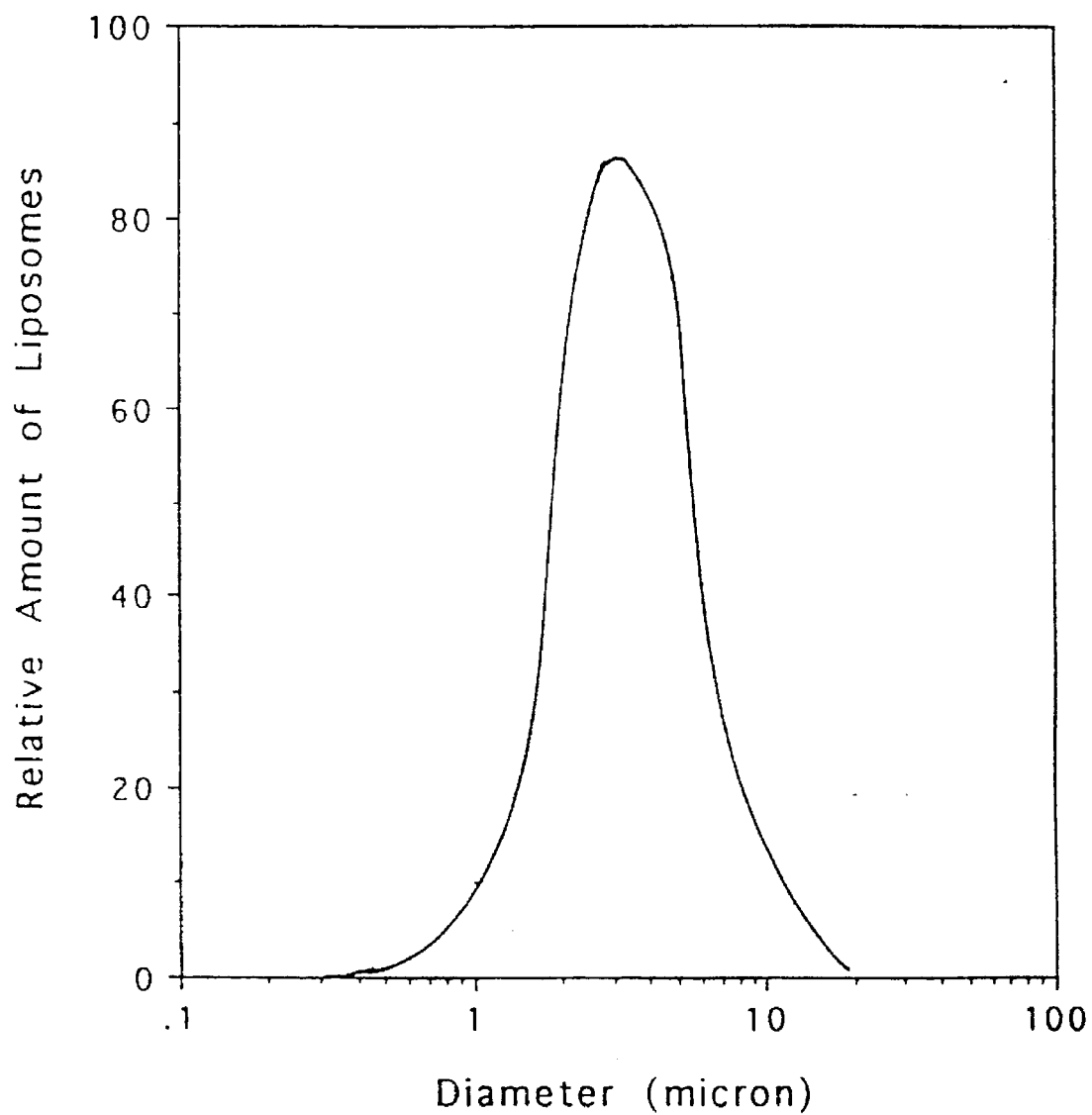
FIG. 1. Size (i.e., diameter in microns) distribution of neutral liposomes (Type A), determined in a Coulter particle analyzer. The size distribution of the prepared liposomes was not significantly altered when the liposomes were formed in a buffer in the presence of 2 mM zinc chloride.

The fibrinogen for use in producing the fibrin glue-containing liposome composition of the invention may be prepared by employing starting materials of varying purities and by following a number of procedures known to those skilled in the art (Blomback, B. and M. Blomback, 1956, *Ark. Kemi.*, 10:415–443; Stryker, M. H. and Waldman, A. A., 1978, *Kirk-Othmer Encyclopedia of Chemical Technology*, Vol. 4, 3rd ed., John Wiley, pp 25–61; Lowe G. D. O. et al., 1987, *Fibrinogen 2: Biochemistry, Physiology and Clinical Relevance, Excerpta Medicus*, Elsevier Science Publishers; Dresdale A., et al., 1985, *Surgery*, 97:750–755; Sponitz W., et al., 1987, *Amer. Surg.*, 59:460–462; and Burnouf-Radosevich, M. et al., 1990, *Vox Sang* 58:77–84). Fibrinogen may be purified from human plasma as a by-product of anti-coagulated red blood cell concentrates from one individual or pooled from many individuals. Cryoprecipitate from fresh frozen plasma is frequently the source of concentrated fibrinogen (A. Dresdale et al., 1985, *Surgery*, 97:750–755) and is suitable for use in the present invention. Preferably, for the invention, fibrinogen is prepared from the fractionation of plasma by an adaptation of the Cohn technique (Blomback, B. and M. Blomback, 1956, *Ark. Kemi.*, 10:415–443; Stryker, M. H. and Waldman, A. A., 1978, *Kirk-Othmer Encyclopedia of Chemical Technology*, Vol. 4, 3rd ed., John Wiley, pp 25–61). The adaptation comprises vital inactivation using solvent-detergent or other techniques, such as UV irradiation, lyophilization, or heating (U.S. Pat. No. 5,116,950 to Miyano, K. et al.).

Despite careful blood donor selection and donor blood screening, a primary concern in the preparation of fibrinogen from human sources is the inactivation of infectious viruses. Lipid coat viruses which are insidiously present in human plasma protein samples are effectively inactivated by treating the plasma or the blood component with organic solvent and detergent mixtures (i.e., SD mixtures), (U.S. Pat. No. 4,540,573 to Neurath A. R. and Horowitz B., 1985; Horowitz, B. et al., 1985, *Transfusion*, 25:516–522; Horowitz, B. et al., 1992, *Blood*, 79:826–831; Piet, M. P. J. et al., 1990, *Transfusion*, 30:591–598; Burnouf-Radosevich et al., 1990, *Vox Sang*, 58:77–84; Horowitz, B. et al., 1992, *Blood*, 79:826–831). If desired, fibrinogen or thrombin sterilized by the SD process may be subjected to additional virucidal procedures and sterilization techniques, such as high temperature treatment (i.e dry heat at about 60° C. to 68° C. for up to 96 hours) or treatment with quenchers (e.g., β-propriolactone or flavinoids such as rutin) and ultraviolet radiation. Further, it is envisioned that procedures which effectively eradicate or inactivate non-lipid coat viruses may also be used to treat the fibrinogen, thrombin, and blood protein components. Although the SD process is highly effective, it is cautioned that not all virucidal treatments are equally effective; nonkilled or non-inactivated viruses are a threat to the safety of the final product. Care must also be taken to ensure that minimal protein degradation occurs during viral inactivation, since the physical properties of the fibrin glue depend upon the absence of degradation or denaturation of the very protein components responsible for its clotting activity (e.g. fibrinogen and thrombin).

In accordance with the invention, human-derived virally inactivated fibrin glue is prepared from several integral and interactive components, which include human fibrinogen and thrombin components that are virtually free from active lipid coat viruses.

To formulate the fibrin glue for use in the invention, virally inactivated, (VI) fibrinogen and thrombin from human sources are present in the fibrin glue composition in appropriate concentrations. For example, Table 1 describes the range of amounts, and the preferred and more preferred amounts of fibrinogen and thrombin (or other activating enzymes), liposomes, and calcium used to formulate fibrin glue in which liposomes are embedded. The resulting concentration of fibrinogen in the final fibrin glue composition is about 10–90 mg/mL, preferably about 30–60 mg/mL, and more preferably about 40 mg/mL, while the concentration of thrombin or other enzyme in the final glue composition is about 1–200 U/mL, preferably about 5–20 U/mL, and more preferably about 10 U/mL.

TABLE 1

|  | Fibrinogen mg/mL | Thrombin U/mL | Liposomes μL/mL | Calcium (Ca(II)) mM |
|---|---|---|---|---|
| Suitable Range | 10–90 | 1–200 | 20–300 | 1–30 |
| Preferred Range | 30–60 | 5–100 | 50–100 | 10–15 |
| Optimal Range | 40 | 10 | 75 | 10 |

The fibrin glue and liposome bioadhesive composition of the invention constitutes a new generation of biological and bioactive sealants, adhesives, or material for fabricating films or coatings. As a result, there is less risk of contaminating agents (e.g. viruses and the like) found in the final composition. In addition, the production of the present fibrin glue containing liposomes is economical to make and use.

Liposomes for use in fibrin glues in general, and in the mixture with fibrinogen in particular, may be formed by a variety of techniques. It is important that the liposomes, however they are produced, do not adversely modify the physical properties of the fibrin glue once they are embedded in the glue. As will be clear from the present invention, the fibrin glue-containing liposome composition is designed not to deter from the clot forming and bioadhesive attributes of the fibrin glue. In fact, the liposomes themselves may favorably modulate the biophysical properties of the fibrin glue by increasing or decreasing the rate of clot formation and gelation, by strengthening or weakening the clot, or by improving the viscoelasticity of the fibrin clot as needed or desired. The techniques available for testing these biophysical properties of fibrin glue have been described (Marx G., 1988, *Thrombos. Haemostas.*, 59:500–503; Marx G. and Blankenfeld, A., 1993, *Blood Coag. and Fibrinolysis*, 4:73–78). It is envisioned that the liposomes may be formulated to entrap a component or components which could modulate the final fibrin glue characteristics. For example, some or all of the liposomes for use in the fibrin glue composition of the invention may be prepared to contain aprotinin or other anti-proteases, such as ε-amino caproic acid (EACA) in their aqueous phase compartment, which, when released at the site of fibrin glue-liposome composition during glue degradation, would slow the rate of protein degradation, thus prolonging the lifetime and viability of the fibrin glue sealant.

The fibrin glue formulated in the presence of liposomes maintains its mechanical properties as determined by breaking strength or tensile strength studies and viscoelasticity studies (e.g., FIGS. 2–6). In the present invention the quality of the biophysical parameters is not significantly modified by the liposomes in the bioactive composition. Indeed, the liposomes are even suitable for improving the quality of the fibrin glue formulated to include such liposomes.

The basic constituents of liposomes are various saturated or unsaturated lipids or phospholipids, with or without the addition of cholesterol and other constituents, such as aliphatic compounds having either amino or carboxylic acid groups. Liposomes of several types suitable for use in the present invention may be prepared by a variety of techniques that may ultimately influence liposome morphology, type, and size. Many techniques for preparing liposomes have been described (Szoka Jr. and Papahaddjopoulos, D. (1980), *Ann. Rev. Biophys. Bioengineering*, 9:467–508; Gregorius G. (Ed). (1983) *Liposome Technology, Vols. I, II, III.*, CRC Press, Boca Raton, Fla. (1991); Ostro (Ed)., *Liposome Preparations: Methods & Mechanisms*, Marcel Dekker Inc. N.Y.; Davis, S. S. and Walker, I. M., (1987), *Methods in Enzymology* 149: 51–64). These methods are applicable for producing liposomes for embedding into the fibrin glue to be applied to a specific tissue site. As but one example, a technique for producing liposomes for use in the invention is by ethanol injection. In this technique, equimolar quantities of cholesterol and hydrogenated lecithin are mixed and warmed to 60° C. in ethanol to form a solution, and the solution is injected in an aqueous buffer at 60° C. containing the material to be encapsulated. The emulsion is incubated 60° C. for one hour, centrifuged at 2000×g for 5 minutes, and the supernatant is removed. The liposomes are suspended in Tris-saline buffer and stored at 4° C.

Liposomes of several types are suitable for use in the present invention. For example, neutral liposomes designated as Type A (described in Example 5) are formulated with equimolar amounts of cholesterol and hydrogenated lecithin and are referred to as neutral liposomes. As described in Example 6, Type B liposomes are formulated with 50% cholesterol, 40% hydrogenated lecithin, and 10% stearyl amine on a molar basis. As a consequence of their composition, Type B liposomes have free amine groups on their surfaces; such groups on Type B liposomes are potentially capable of affecting certain biophysical parameters of the fibrin glue composition. Type C liposomes, described in Example 7, are formulated with 50% cholesterol, 40% hydrogenated lecithin, and 10% stearic acid on a molar basis. Type D liposomes are formulated with 50% cholesterol, 40% hydrogenated lecithin, and 10% diethylstearylamine on a molar basis. Depending on pH, exemplary liposomes of the B and C types contain electrically-charged chemical moieties on their surfaces.

Large liposomes (e.g. multilamellar vesicles having a diameter size range of 0.1 to 5 to >10 μm, and large unilamellar vesicles having a diameter size of ≧0.06 μm) and small liposomes (e.g. small unilamellar vesicles having a diameter size of about 0.02 to 0.05 μm) may be employed in the present invention and may be produced by conventional methods as previously indicated. Although those skilled in the art will appreciate that virtually all types of liposomes are suitable for use in the present invention, some liposome types may have particular properties which make them especially conducive to forming a stable and effective fibrin glue-liposome bioadhesive. For example, as described above, neutral liposomes of 5 μm diameter with a good load capacity (e.g. at least about 10% to 20% aqueous phase) may be preferred so as to provide adequate amounts of entrapped materials at the site of action and so as not to interfere substantially with the crosslinking properties of the fibrin glue after application at the site.

In accordance with the invention, the contents of the liposomes are routinely entrapped in the aqueous phase, rather than within the membrane bilayer of the liposome. The amount of aqueous phase containing bioactive material incorporated into the aqueous interior compartments of the liposomes for effective use in the invention was tested by forming Type A liposomes in Tris buffer (Tris-saline buffer, pH 7.4) containing 2 mM $Zn^{2+}$. The $Zn^{2+}$ which remained after washing the liposomes was measured by X-ray fluorescence (Gorodetsky, R., Mou, X., Blankenfeld, A., and Marx, G., 1993, *Amer. J. Hematol.*, 42:278–283). From these measurements, it was estimated that the liposomes contained, on a volume per volume basis, about 10% to 20% aqueous phase, which is indicative of the "load" of the liposomes. The loaded liposomes were stable at both 4° C. and 22° C., and they retained their aqueous phases quite well over a period of several weeks. Such $Zn^{2+}$ containing liposomes were used in in vivo studies in accordance with the invention (Example 10).

Knowing the liposome load allows the calculation of the effective concentration or fraction of reagent(s) entrapped (i.e., contained) within the aqueous phase for effecting delivery and deposit of the load at the site of a wound or opening. A typical load is calculated on the basis of the orginal amount of the aqueous starting material used and the final amount of material that is contained in the liposome. As a specific but non-limiting example, the $Zn^{2+}$ solution served as a quantifiable marker for the entrapped contents of the liposomes. Thus, the amount of $Zn^{2+}$ in the starting solution is determined (e.g., 130 ppm). The liposomes are formulated to entrap a portion of the $Zn^{2+}$ solution. The fractional liposome volume is determined from a particle counter. The liposomes so formulated are washed in buffer. After washing, the aqueous phase is removed and the amount of $Zn^{2+}$ that has been entrapped into the liposome is measured.

Using 300 μL of liposomes containing 2 mM $Zn^{2+}$ solution in their interiors would translate overall into 60 μM $Zn^{2+}$ in 1 mL of fibrin glue at and around the site of the wound. The liposomes can fuse with cells at the site of the wound and thereby merge their aqueous contents with the contents of cells. Thus, the aqueous phase of the liposome is delivered to the wound site where it subsequently diffuses into and around the site of application.

Another aspect of the invention involves the use of fibrin glue containing light sensitive or photoactivatable liposomes (LSL), which may provide more controlled release of their contents into the environment over time. Such liposomes can also be prepared to contain bioactive materials, additives, and medicaments, and are kept in a light-protected (e.g. filtered) container until use. When used in fibrin glue, a light source (e.g., ultraviolet light or laser) are focussed on the LSL, thereby causing them to release their contents into the surroundings at the site of application. Light sensitive and photoactivatable liposomes are prepared essentially as described for non-light sensitive liposomes; they are virtually identical, but they provide for manipulated, light-controlled release of their contents. Light sensitive liposomes may be prepared by using lecithins of retinoic acid (such as 1,2-diretinoyl-sn-3-glycerophosphocholine (DRPC), 2-retinoylysolectin (LRPC) or 1-palmitoyl-2-retinoyl-sn-3-glycerophosphocholine (PRPC) in the lipid and cholesterol mixture, as described (Pidgeon, C. and Hunt, C. A., 1987, *Methods in Enzymol.* 149:99–111). Mixtures of DRPC/LRPC in ratio ranges of about 70:30 to about 30:70 are used to formulate light sensitive liposomes. Some formulations might include up to 40% added α-tocopherol (α-T) to help in forming the light-sensitive liposomes. Preparations of LSL would necessarily be kept in the dark to prevent light induced degradation of the liposome structures and the release of their aqueous compartments. The light-sensitive liposomes are mixed with fibrin glue components (i.e., fibrinogen or thrombin) of the fibrin glue and liposome composition to allow their compartments to be released when desired by exposure to the chosen light source.

Alternatively, the glue component, thrombin, is incorporated into the LSL. Such thrombin-containing liposomes are then mixed directly with fibrinogen in a light filtered container. The release of thrombin would be instigated by exposing the mixture to the appropriate light source. Thus, a single-compartment delivery system could be devised for fibrin glue application, with clotting only initiated by exposure to the activating light source.

Bioactive agents contained in liposomes of the fibrin glue-containing liposome composition The liposomes of the invention are designed to contain, carry, and release biologically active agents in accordance with the internal load or capacity of the liposomes. It is envisioned that liposomes containing biologically active substances and medicaments and embedded in the fibrin glue will carry and release their contents at a wound site or surgical or nonsurgical opening in animals, including humans, to aid in the healing and protection process following all types of surgical or wound healing procedures and applications. Examples of applications for the "loaded" liposomes in fibrin glue include, but are not limited to, partial or complete replacement of sutures in skin grafts, burns or ulcers, or surgical and nonsurgical openings; nerve and vessel anastomoses; surgery of soft tissues, such as parenehymal tissues of liver, lung, or spleen; microsurgeries in all areas of the body; orthopedic surgeries for tendon repair and bone or cartilage grafting, general surgeries, such as cuts and laceration repair; cardiovascular surgery for vascular grafts and anastomoses; thoracic surgery to seal duct leaks and esophageal anastomoses; otolaryngology-head and neck surgery; ophalmological surgeries, general dental use and surgeries; general surgeries in various anatomical body parts and sites.

A wide variety of biologically active agents as well as medicines and pharmaceuticals may be contained within the liposomes of the fibrin glue-liposome formulation. Examples of various agents to be entrapped in the liposomes include, but are not limited to, drugs, neuroleptics, vitamins (e.g. Vitamin C, (i.e. ascorbic acid or ascorbate), Vitamin A, Vitamin E, Vitamin D, Vitamin B, or derivatives thereof), growth factors (e.g. lymphokines, cytokines), hormones, steroids, glucocorticosteroids, antibiotics (e.g. penicillin, gentimycin, erythromycin, adriamycin, tobramycin), antibacterial compounds, including bacteriocidal and bacteriostatic compounds, antiviral compounds, antifungal compounds, antiparasitic compounds, tumoricidal compounds, tumoristatic compounds, toxins, enzymes, enzyme inhibitors, proteins, peptides, minerals (such as zinc or copper), neurotransmitters, lipoproteins, glycoproteins, immunomodulators, immunoglobulins and fragments thereof, dyes, radiolabels, radiopaque compounds, fluorescent compounds, fatty acid derivatives, polysaccharides, cell receptor binding molecules, anti-inflammatories, antiglaucomic compounds, mydriatic compounds, anesthetics, nucleic acids (e.g. RNA and DNA fragments), and polynucleotides. It is also envisioned that selected fragments, portions, derivatives, or analogues of some or all of the above may be used, when practical, as additives in the aqueous phase of the liposomes of the invention. In addition, lipophilic drugs or other compounds may be incorporated into the phospholipid membrane of the liposomes.

The invention is suitable for multiple bioactive agents to be contained in liposomes used in the fibrin glue bioadhesive composition. Should such a utility be desired, two or more bioactive agents may be entrapped in one liposome type which forms an integral part of the fibrin glue, and becomes subsequently embedded or deposited in the glue clot. Alternatively, two or more different types of liposomes or mixtures of liposome populations, each of which entraps the same or different bioactive agents, may be embedded in the fibrin glue-liposome composition. Different preparations of liposomes may comprise monophasic lipid vesicles (i.e. those having unilamellar lipid bilayers) or plurilamellar vesicles (i.e. those having multilamellar lipid bilayers), such as have been described previously (M. Schafer-Korting et al., 1989, *J. Am. Acad. Dermatol.*, 21:1271–1275; U.S. Pat. No. 4,708,861 to M. C. Popsecu et al.). As envisioned for use in the present fibrin glue and liposome composition, one type of liposomes (e.g. neutral liposomes) is formulated to entrap a particular bioactive material and a second type of liposomes (either the same type as the first or a different type) is formulated to entrap another bioactive material. Both types of liposomes containing their respective bioactive contents are mixed with the components comprising fibrin glue, and the resulting fibrin glue and liposome composition contains two types of liposomes capable of delivering their respective bioactive contents at the incision or wound or opening site. It is apparent that mixtures of different types of liposomes containing a variety of bioactive materials may be formulated and embedded in the composition.

Fibrin glue-containing liposome formulations

As described hereinbelow, liposomes may be suspended in either a fibrinogen or thrombin solution and stored at temperatures from about 4° C. to about 37° C. prior to use. Alternatively, individual mixtures of liposomes and either fibrinogen or thrombin preparations may be frozen at −70° C. or lyophilized by drying in vacuo at about −30° C. Prior to use, the mixtures are reconstituted in water or buffer such as Tris-saline. All of the methods of storage result in viable, long-lasting liposome glue compositions following reconstitution of the stored materials.

In accordance with the invention, liposomes formulated with fibrin glue in a variety of modes result in liposome-containing fibrin glue in which liposomes are embedded and deposited in the clotted fibrin glue bioadhesive. Because fibrin glue forms the environment for deposition of the liposomes, the glue localizes the liposomes at the site or sites of application.

An advantage of the fibrin glue of the invention is that it is physiologically compatible with biological systems for in vivo use, such that both it and the liposomes contained therein, provide beneficial effects for the recipient animal without being toxic. Similarly, another advantage of the fibrin glue-liposome compositions is that the liposome-glue will remain in clotted form in the environment in which it is administered or applied due to the formulations of present compositions of the invention, and will withstand physiological body temperatures and the conditions of the host environment in vivo. Because they comprise phospholipids and cholesterol, the liposomes of the composition will also be naturally metabolized over time by absorption by cells and tissue (reviewed by Schater-Korting M., Korting H C. and Braun-Falco, O. J., 1989, *Amer. Acad. Dermatol.* 21: 1271–1275). It is clear that the fibrin glue allows for controlled localization and the release of the contents of the embedded liposomes into the desired tissue site.

In one embodiment of the invention, fibrinogen, thrombin, and liposomes are each stored separately, and then are mixed together when desired, for use to form the fibrin glue-liposome composition at the site of the surgical or nonsurgical wound or opening. By way of example, lyophilized fibrinogen (about 50–70 mg) and thrombin (about 20–40 U) were each reconstituted in an appropriate buffer (e.g., about 1 milliliter of 10 mM Tris-saline, pH 7.4) to form a fibrinogen solution and a thrombin solution. Thereafter, about 200 μL of liposomes were added to the fibrinogen solution which was mixed gently to form a fibrinogen-liposome suspension. The above solutions were formulated in syringes and the steps to mix the component solutions were carried out in syringes. The fibrinogen and liposome suspension were applied simultaneously, along with the thrombin solution, to the site of the wound. The fibrin glue that formed within minutes contained about 10% embedded liposomes and provided a liposome-containing bioadhesive at the wound site. On average, about 1% to about 20% by volume), more preferably about 2% to about 15% (by volume), and most preferably, about 5% to about 10% (by volume) of liposomes were embedded in the fibrin glue to produce the fibrin glue and liposome bioadhesive of the invention. The amount of liposomes in the composition represent the volume per volume percentage of liposomes in the final fibrin glue and liposome formulation.

In another embodiment, liposomes are pre-mixed with a solution of fibrinogen, and stored at 4° C. The liposome and fibrinogen mixture can be lyophilized, if desired, prior to storage. Prior to or at the time of use, the mixture of liposomes and fibrinogen is warmed to 37° C. and mixed with thrombin solution at the site of injury or opening, thereby forming the fibrin glue composition in which the liposomes are entrapped.

In another embodiment, liposomes are pre-mixed with a solution of thrombin, and stored at 4° C. Prior to or at the time of use, the mixture of liposomes and thrombin is mixed with reconstituted fibrinogen solution at the site of the surgical or nonsurgical wound or opening, thereby forming liposome-containing fibrin glue.

In accordance with the invention, the fibrinogen and thrombin solutions are each stored in separate receptacles or containers (e.g. syringes) prior to use or mixing in the fibrin glue-liposome composition. Liposomes may be suspended in a fibrinogen solution in a first syringe, and then mixed with the thrombin solution from a second syringe on or around the site of the wound or opening. Alternatively, liposomes may be suspended in a thrombin solution in a first syringe, and then mixed with fibrinogen solution from a second syringe at or around the wound site or opening.

In vivo and other uses of fibrin glue-containing liposome composition

The fibrin glue-liposome composition of the present invention may be used for immediate or sustained release of a biologically active substance or medicament both in vitro and in vivo. For in vivo use at a surgical or nonsurgical site, the fibrin glue-liposome composition may be formulated in the number of ways elucidated above. In brief, the fibrin glue components and liposomes, however they are pre-mixed, may be added together at or over the wound site at the desired time of use. Consequently, the fibrin glue-liposome bioadhesive is formed in situ following the admixture and administration of all of the components at the site. Administration is preferably topical and includes, but is not limited to, application on, at, around, or near areas such as eyes, skin, ears, or on afflictions such as wounds, burns, surgical and nonsurgical openings, fissures, ulcers, blisters, bone breaks, and the like. The present invention is particularly useful for such treatments in which the release over time of antibiotics or healing, prophylactic, or therapeutic medicaments would assist in the healing and recovery process. In addition, because the biochemical action of fibrin glue mimics a part of a normal biological process, the fibrin glue-liposome composition may be used to promote hemostasis by controlling hemorrhaging, to seal and bond tissue, and to support wound healing. Similarly, the fibrin glue-containing liposome composition may be topically administered at the site of burns in which the release of antimicrobials, cell growth factors, and/or medicaments is also of critical importance in the promotion and speed of the healing process.

Fibrin glue containing liposomes can be also be used to bind bone fragments. The bone-binding ability of the fibrin glue and liposome composition is very useful in bone reconstruction, as in plastic surgery or the repair of major bone breaks. For example, a bone fracture can be sealed with the fibrin glue and liposome composition so that the glue both seals the break and entraps and localizes the liposomes which are formulated to contain bone-specific growth factors. Upon slow dissolution of the fibrin glue at the site of the bone fracture, the liposomes release their entrapped growth factors and thus improve the rate and quality of the healing bone.

For facial reconstruction, autologous bone from a patient can be ground or made into powder or the like, added to fibrinogen mixed with liposomes, and mixed into a paste. Thrombin is then mixed with the fibrinogen and liposome paste in an amount sufficient (i.e., 1 U/mL) to allow the paste to be applied to the desired locale, where the fibrin glue and liposome composition finally congeals. The amount of time for the congealing of the composition to occur can be controlled by adjusting the level of thrombin used. The liposomes can be formulated to contain bone growth factors (for example, as described in Sampath T. K. et al., 1992, *J. Biol. Chem.*, 267:20352 and Wang E. et al., 1990, *Proc. Natl. Acad. Sci. U.S.A.*, 87:220) or antibiotics in their aqueous phases. One skilled in the art will appreciate that the types of liposomes (e.g., neutral or charged) and the choice of aqueous phase components can be chosen as desired.

Fibrin glue containing liposomes can also be fabricated as a film or membrane. Such films or membranes are advantageous to cover large surface areas. In addition, the fibrin glue and liposome compositions can be employed to fabricate implantable devices which include not only films, but also foams or chunks of the congealed fibrin glue and liposome composition. The films and devices may be formed ex vivo by application as liquids or sprays for subsequent implantation or use in vivo after gelation. Such fibrin glue-containing liposome compositions may be also be used to coat devices, such as prosthethic devices, catheters, or valves, and the like, which would be temporarily inserted or permanently implanted into an animal or human patient.

For the purposes of the invention, the fibrin glue film (or membrane) is defined as a thin layer whose thickness can range between 0.1 mm to 5 mm. Such fibrin glue films exhibit a high degree of viscoelasticity and can be reversibly twisted and stretched up to 4 times their initial dimensions before breaking. Fibrin glue films containing Type A, B, or C liposomes which entrap biologically active compounds within their aqueous phases, are suitable for use in the invention. For example, fibrin glue film containing Type A, B, or C liposomes can be sprayed onto a hydrophobic surface, such as Parafilm (American Can Co.) to form a fibrin glue and liposome film or membrane, which does not adhere permanently to the surface. After setting or cross-linking for about 1 hour, the fibrin glue film formulated with its entrapped liposomes is peeled away from the parafilm surface and exhibits physical characteristics virtually identical to fibrin glue film formulated without liposomes. The combination of fibrin glue film and liposomes can impart beneficial biological effects to such films used as described above for formation in situ. The results of producing a film comprising the fibrin glue and liposome compositions is described in Example 12.

Fibrin glue film containing liposomes can also be used to coat or to layer over a variety of materials used to make prosthetic devices for implantation. In an embodiment of this invention, fibrin glue containing liposomes can be sprayed or applied as liquid onto a metal surface or other substrate onto which the composition adheres tightly. For example, a fibrin glue film containing Type A liposomes sprayed onto aluminum foil bound very tightly. Alternately, the film could be formed by layering the fibrin glue and liposome mixture onto the surface or substrate. When aluminum foil was used as the substrate, the film (about 1 mm thick) could not be easily peeled or removed from the aluminum surface (FIG. 10), while the same film deposited on the a hydrophobic surface was easily removed. These examples serve to illustrate, but not to limit, the further embodiments of the invention in which Types A, B, or C liposomes are incorporated into fibrin glue film deposited onto a synthetic surface prior to use in animals or humans.

EXAMPLES

The examples herein are meant to exemplify the various aspects of carrying out the invention and are not intended to limit the invention in any way.

EXAMPLE 1

Preparation of Fibrinogen from Cryoprecipitate

Although fibrinogen for use in the bioadhesive composition of the invention may be prepared by several techniques as disclosed above, specific and non-limiting examples of fibrinogen preparation are provided. Using cryoprecipitate as a source of fibrinogen is suitable for formulating the fibrin glue and liposome composition of the invention. Alternatively and oftentimes more preferably, fibrinogen is desired in a more purified or concentrated form, and thus is prepared in accordance with the Cohn fractionation method described in Example 2.

Cryoprecipitate was prepared according to the American Association of Blood Bank (AABB) protocol as published in Walker, R. H. et al., 1990, *Technical Manual, American Association of Blood Banks*, 10th Edition, Arlington, Va. Briefly, a unit of fresh-frozen human plasma was placed in a 0°–4° C. water bath for 1 to 1½ hours (or until thawed). The thawed plasma was centrifuged at 5000×g for 5 minutes 4° C. The supernatant was removed, leaving about 10 to 20 mL of plasma mixed with the cryoprecipitate, or concentrated fraction containing a complex mixture of clotting proteins, including fibrinogen, albumin, antihemophilic factors, and other proteins (see Table 2). The cryoprecipitate was warmed to 37° C. for 15 minutes prior to use in the fibrin glue and liposome composition.

TABLE 2

Biochemical Composition of Cryoprecipitate Prepared from Fresh-Frozen Plasma ("FFP Cryo")

|  | FFP Cryo |
| --- | --- |
| Yield (g) | 11–16 |
| Protein (mg/g) | 60–80 |
| Fibrinogen (mg/g) | 9–30 |
| IgG (mg/g) | 10–14 |
| Factor XIII (U/g) | 4–9 |

Mean values n = 10

One skilled in the art will appreciate that cryoprecipitate prepared from flesh-frozen plasma is suitable for use in the bioadhesive composition containing liposomes, as is a more purified preparation of fibrinogen such as that obtained from, but not limited to, the Fraction I paste of the Cohen fractionation method as described above and known to those in the art.

EXAMPLE 2

Preparation of Fibrinogen from Fraction I Paste of Cohen Fractionation

Fibrinogen was prepared from Fraction I paste cold ethanol plasma fractionation (Blomback, B. and Blomback, M., 1956, *Ark Kemi*, 10:415–443; Stryker, M. H. & Waldman, A. A., 1978, *Kirk-Othmer Encyclopedia of Chemical Technology*, Vol 4, 3rd ed., pp 25–61, John Wiley; Lowe G. D. O. et al., 1987, Fibrinogen 2: Biochemistry, Physiology and Clinical Relevance. Excerpta Medicus, Elsevier Science Publishers). The Fraction I paste was slurried in cold (4° C.) Tris-saline buffer containing 2 mM EDTA, pH 6.5, and the supernatant discarded. The residual paste was dissolved in warm (37° C.) Tris-saline buffer containing 2 mM EDTA to form a solution, and the solution was either filtered or centrifuged at 5000×g for 15 minutes. The solution was cooled to 14° C. Cold 50% ethanol was then added slowly and the ethanol-containing mixture was cooled to 4° C. over a 1 hour period. The precipitated fibrinogen was collected by centrifugation at 3000×g for 15 minutes, and was dissolved in Tris-saline buffer, pH 7.4. Following this step, the purified fibrinogen was either stored at −30° C. or was lyophilized. Thawed fibrinogen or fibrinogen reconstituted by adding water or buffer was mixed with liposomes of Types A, B, C, or D, as desired, without precipitation or gelling of the resulting fibrinogen and liposome mixture.

EXAMPLE 3

Preparation of Virally-Inactivated (VI) Fibrinogen and Thrombin

Viral inactivation of lipid-coat viruses was achieved by employing the solvent detergent (SD) method. To achieve SD viral inactivation, 1% Tween 80 (Triton X-100, sodium cholate, or other nonionic detergents may also be used) and 0.3% tri(n-butyl)phosphate (TNBP) were added to the fibrinogen preparation and kept at 24°–30° C. for 4 hours to result in SD fibrinogen. In the Fraction I paste method, viral inactivation was performed prior to precipitation with 7–10%, by volume, of cold ethanol. The TNBP solvent and Tween 80 detergent reagents were removed by repeated (2 times) precipitation of the fibrinogen with 7–10%, by volume, of cold ethanol (Burnouf-Radosevich et al., 1990,

*Vox Sang*, 58:77–84) and resolubilized in a buffer of physiologic pH and ionic strength. The complete SD procedure resulted in acceptable viral kill (on the order of greater than $10^5$ logs) and low amounts of residual viral inactivating reagents in the final SD fibrinogen preparation.

Laboratory scale preparations of fibrinogen, including SD fibrinogen, for use in the bioadhesive liposome and fibrin glue compositions typically contained the following constituents as indicated. The fibrinogen constituents are provided as a guide and are not meant to limit the invention in any way. For example: Fibrinogen (Fib): 20–80 mg/mL; Factor XIII (FXIII): 2–12 U/mL; Fibronectin (FN): <1%; Albumin (Alb): <1%.

Bovine or human thrombin were employed for inducing gelation or clotting of fibrin glue. Those skilled in the art will appreciate that, at the present time in the U.S., bovine thrombin is commercially available and is the type of thrombin that is licensed for clinical use in the U.S. However, human thrombin sources are also suitable for use in the invention provided that the human thrombin is appropriately purified and virally inactivated.

The human thrombin used for instigating cross-linking of the components of the fibrin glue in the invention was obtained by activating prothrombin from Cohn Fraction III paste by established techniques (Fenton II, J. W. et al., 1977, *J. Biol. Chem.*, 252:3587–98; Crowley, C., European Patent Application No. 0 439 156 A1; U.S. Pat. No. 4,696,812 to Silbering S. B. et al. (1987); U.S. Pat. No. 4,965,023 to Silbering S. B. et al., (1990)). Briefly, prothrombin, prepared from Cohn fraction III paste, was activated by incubation with 20–30 mM Ca(II) and a prothrombin activating amount of thromboplastin. The resulting solution was filtered and passed over a DEAE-Sepharose column to remove contaminating proteins. The eluate was then passed over a CM-Sepharose column and the eluate was discarded. The bound thrombin was eluted with higher ionic strength buffer (e.g. 0.5N NaCl in PBS, pH 6.5 to 8.0). Other variations of this process have been described (see Crowley et al., European Patent Application No. 0 439 156 A1). Other methods of activating prothrombin may be employed. The resulting purified thrombin can be vitally inactivated by a variety of methods including SD, heat, or UV irradiation, with or without quenchers. The purified thrombin maintained its enzymatic activity, even following viral inactivation treatment. In addition, mixing purified thrombin alone with liposomes of Types A–C as disclosed herein did not significantly alter its enzymatic or clot-inducing activity.

When mixed together, the vitally inactivated fibrinogen and thrombin components became coagulated and formed fibrin glue.

EXAMPLE 4

Preparation of Liposomes

To prepare liposomes containing a different lipids and cholesterol via the ethanol injection technique, equimolar quantities of cholesterol (Chol) and hydrogenated lecithin (HL) were dissolved in 100 µL of absolute ethanol 100 µL chloroform and mixed at 60° C. for 10 minutes and then injected into a 10-fold larger concentration of Tris-saline buffer, pH 7.4, containing the material to be entrapped in the aqueous phase of the liposome. Some liposomes were also made with stearyl amine (B) or stearic acid (C) or diethylstearylamine added to the alcohol phase in one-tenth molar quantities relative to the amounts of Chol and HL used. Following the addition of all of the liposome reagents to the aqueous phase, the mixture was incubated an additional 1 hour at 60° C., and then treated in an ultrasonic bath for 5 minutes. After ultrasonification, liposomes were cooled to 22° C. for 1 hour, centrifuged at 2000×g for 10 minutes, washed in Tris-saline buffer, pH 7.4, and re-centrifuged two times more before storage at 4° C. Evaluation of the prepared liposomes in a Coulter particle sizer (the Coulter Company) showed unimodal distribution of particles with a diameter range of from about 0.9 to 10 microns, with a mean diameter of about 2.5 microns (FIG. 1)

EXAMPLE 5

Preparation of "Neutral" or "Type A" Liposomes

For the preparation of neutral or type A liposomes containing zinc, 160 milligrams (mg) of hydrogenated phosphatidylcholine (HPC) or L-α-lecithin, (Avanti Polar Lipids, Birmingham, Ala.) were mixed with 40 mg of cholesterol (Chol), absolute ethanol (100 µL), and chloroform (100 µL) and incubated at 60° C. for 15 minutes. For preparation of exogenous materials to be entrapped in the liposome, a solution of 5 mL of aqueous buffer (e.g. Tris-saline buffer: 20 mM Tris, 0.15N NaCl, pH 7.4) containing the material to be entrapped (e.g. 2 mM zinc chloride) was warmed to 60° C. While this solution was stirred with a magnetic stir-bar, the HPC and Chol solution was added and vortexed for about 1 minute. The resulting mixture was incubated at 60° C. for about 1 hour. The mixture was then cooled to 22° C. and centrifuged at 2000×g for 5 minutes to settle the liposomes to the bottom of the tube. The supernatant solution was removed after centrifugation, and the liposomes were washed in Tris-saline buffer, pH 7.4. After washing, the liposomes were again centrifuged and the wash supernatant was removed. The prepared liposomes were analyzed in a cell counter or particle analyzer to determine that their size (i.e. in terms of liposome volume) was in the range of about 4 to about 12 fL, with an mean of about 7 fL. The washed liposome zinc content was determined by x-ray fluorescence spectrometry. A liposome suspension, in which liposomes constituted 14% of the volume, resulted in a zinc value of 20.5 ppm zinc compared with the wash buffer control supernatant which gave a value of around 3 ppm zinc. The prepared neutral liposomes were stored at 4° C. until use.

EXAMPLE 6

Preparation of "Amine" or "Type B" Liposomes

For the preparation of amine or type B liposomes, 160 milligrams (mg) of hydrogenated phosphatidylcholine (HPC) or lecithin, (Avanti Polar Lipids, Birmingham, Ala.) were mixed with 40 mg of cholesterol (Chol), and 2.7 mg of stearyl amine, absolute ethanol (100 µL), and chloroform (100 µL). The resulting mixture was incubated at 60° C. for 15 minutes. For preparation of exogenous materials to be entrapped in the liposome, a solution of 5 mL of aqueous buffer (e.g. 20 mM Tris, 0.15N NaCl, pH 7.4) containing the material to be entrapped (e.g. zinc chloride) was warmed to 60° C. While this solution was stirred with a magnetic stir-bar, the HPC and Chol solution was added and vortexed for about 1 minute. The resulting mixture was incubated at 60° C. for about 1 hour. The mixture was then cooled to 22° C. and centrifuged at 2000×g for 5 minutes to settle the liposomes to the bottom of the tube. The supernatant solution was removed after centrifugation and the liposomes were washed in Tris-saline buffer, pH 7.4. After washing, the liposomes were again centrifuged and the wash supernatant was removed. The prepared liposomes were analyzed in a cell counter or particle analyzer to determine that their size (i.e. in terms of liposome volume) was in the range of about 4 to about 12 fL, with an mean of about 7 fL. The prepared amine liposomes were stored at 4° C. until use.

EXAMPLE 7

Preparation of "Carboxylic Acid" or "Type C" Liposomes

For the preparation of carboxylic acid or type C liposomes, 160 milligrams (mg) of hydrogenated phosphatidylcholine (HPC) or lecithin, (Avanti Polar Lipids, Birmingham, Ala.) were mixed with 40 mg of cholesterol (Chol), and 2.7 mg of stearic acid, absolute ethanol (100 µL), and chloroform (100 µL). The resulting mixture was incubated at 60° C. for 15 minutes. For preparation of exogenous materials to be entrapped in the liposome, a solution of 5 mL of aqueous buffer (e.g. Tris-saline buffer: 20 mM Tris, 0.15N NaCl, pH 7.4) containing the material to be entrapped (e.g. 2 mM zinc chloride) was warmed to 60° C. While this solution was stirred with a magnetic stir-bar, the HPC and Chol solution mixture was added and vortexed for about 1 minute. The final mixture was incubated at 60° C. for about 1 hour, cooled to 22° C., and centrifuged at 2000×g for 5 minutes to settle the liposomes to the bottom of the tube. The supernatant solution was removed after centrifugation and the liposomes were washed in Tris/saline pH 7.4 buffer. After washing, the liposomes were again centrifuged and the wash supernatant was removed. The prepared liposomes were analyzed in a cell counter or particle analyzer to determine that their size (i.e. in terms of liposome volume) was in the range of about 4 to about 12 fL, with an mean of about 7 fL. The prepared carboxylic acid liposomes were stored at 4° C. until use.

EXAMPLE 8

Figure 2:
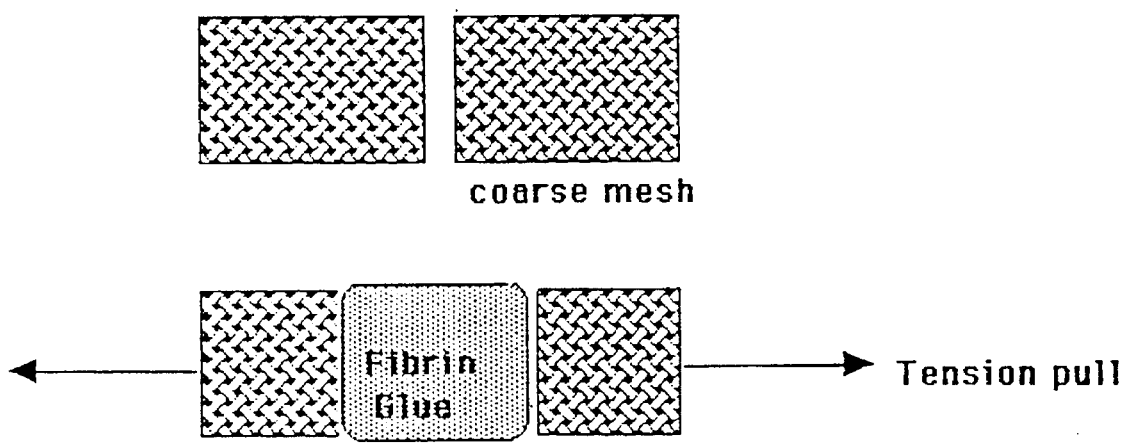
FIG. 2. Schematic diagram for experimentally determining the breaking or tensile strength ("BS" or "TS") of fibrin glue gel. See also FIG. 10.

Effects of Liposomes on the Breaking Strength, BS, (or Tensile Strength) of Fibrin Glue The breaking strength of the fibrin glue in the present fibrin glue and liposome composition was measured by mixing fibrin glue components in a plastic test tube and pipeting the still-liquid mixture into the interface of two pieces of coarse synthetic mesh (0.4 thick by 1 cm wide), (FIG. 2). The fibrin glue was allowed to gel, such that the resulting glue as formulated was totally interwoven between the two pieces of coarse mesh (Marx, G. and Blankenfeld, A., 1993, *Blood Coag. Fibrin.*, 4:73–78). After 2 hours, the Factor XIIIa-induced cross-linking reaction had occurred and the mesh-fibrin-mesh ensemble was pulled apart. The breaking strength was measured as grams per 0.4 cm$^2$ cross-section. In such a test system, the breaking strength of fibrin glue that had been activated with thrombin exhibited a linear correlation with the concentration of fibrinogen, i.e., [Fib], as described by the following equation:

$$BS = slope \times [Fib]$$

The effects of ionic strength and pH on fibrin glue breaking strength were examined. It was found that breaking strength plateaued above 0.1N NaCl and was maximum at pH 7.4. It was also determined that even using cryoprecipitate, which is known to be less pure than purified fibrinogen, the breaking strength was directly related to the levels of fibrinogen.

Figure 3:
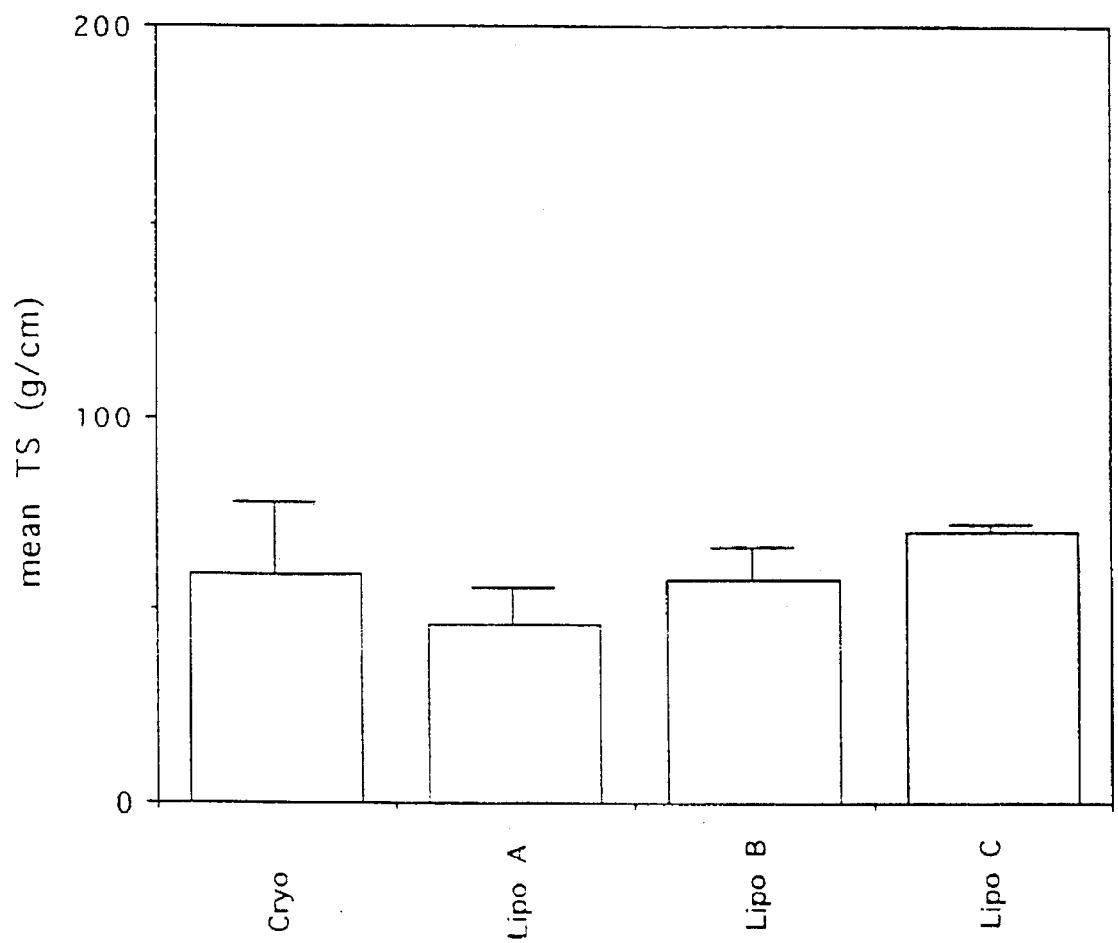
FIG. 3. Breaking strength (i.e., tensile strength, "TS") of fibrin glue (made from cryoprecipitate ("Cryo") as the source of fibrinogen and thrombin with and without 5% (v/v) of neutral (Type A) liposomes ("Lipo A"), amino (Type B) liposomes ("Lipo B"), or carboxylic acid (Type C) liposomes ("Lipo C"). Fibrin glue was formulated using 10 U/mL of thrombin and 10 mM $Ca^{2+}$.
Figure 4:
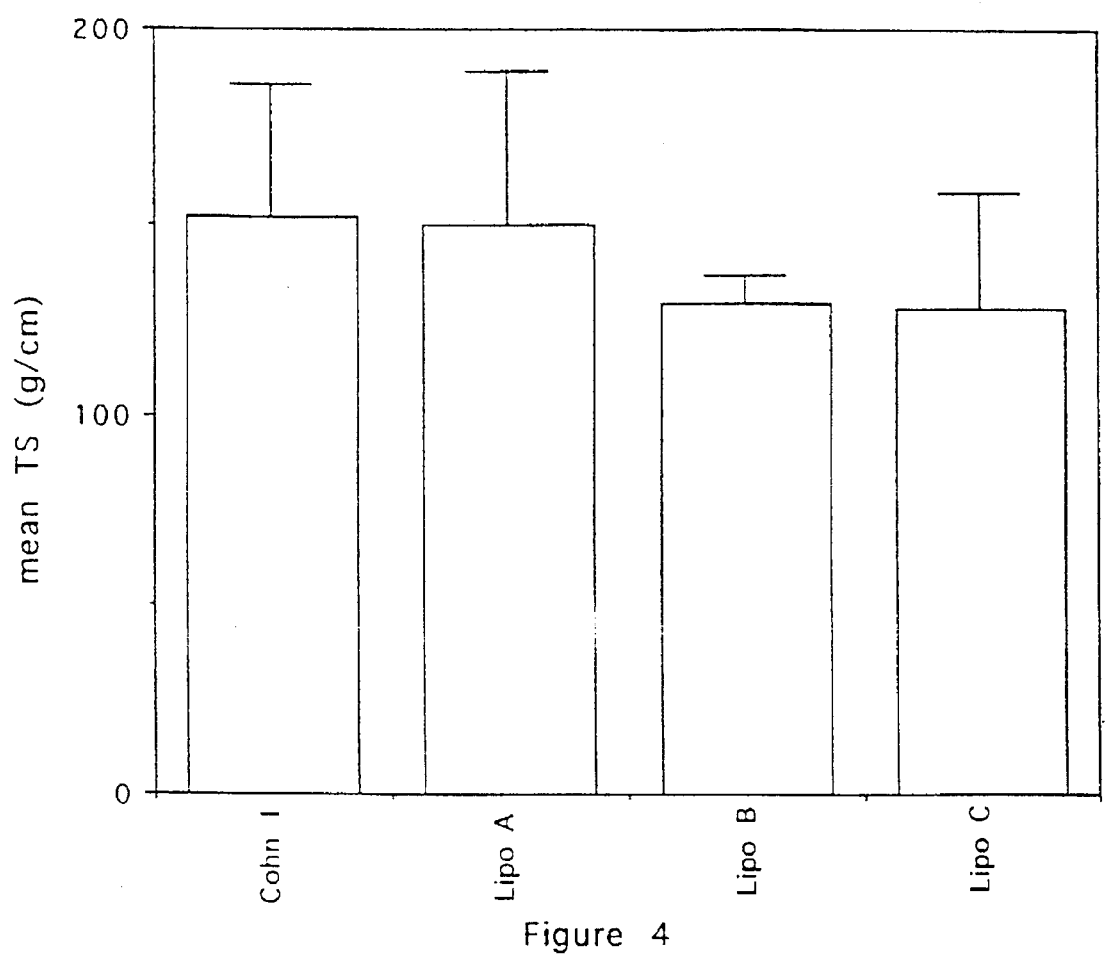
FIG. 4. Breaking strength (i.e., tensile strength, "TS") of fibrin glue formulated with purified fibrinogen (i.e., Fraction I paste of Cohn preparation) and thrombin without ("Cohn 1") and with 5% (v/v) of neutral (Type A) liposomes, "Lipo A"; amino (Type B) liposomes, "Lipo B"; or carboxylic acid (Type C) liposomes, "Lipo C". Fibrin glue was formulated using 10 U/mL of thrombin and 10 mM $Ca^{2+}$.

This system of measuring and determining the breaking or tensile strength of fibrin glue was useful for measuring the effects of the various types of liposomes on the mechanical properties of fibrin glue formed from cryoprecipitate or fibrin glue formed using pure fibrinogen (e.g., from Cohen Fraction I paste), (FIGS. 3, and 4). The results showed that a particular type of liposome was made and added to the fibrin glue components to form the fibrin glue composition at levels which did not significantly affect the mechanical properties and integrity of the fibrin glue formulation. Thus, liposomes can be added to the fibrin glue to produce the compositions of the invention in which the glue has a particular mechanical strength that is suitable for wound and incision closure and healing.

EXAMPLE 9

Viscoelastic Effect of Liposomes in Fibrin Glue

After the onset of gelation, fibrin glue develops viscoelastic properties which can be monitored in a thromboelastograph as TEG amplitude. Tests with Type A, B and C liposomes, as described above, indicated that depending on the composition and proportions of components in the final fibrin glue composition, the liposomes may or may not significantly affect the viscoelasticity of the fibrin glue.

Figure 5:
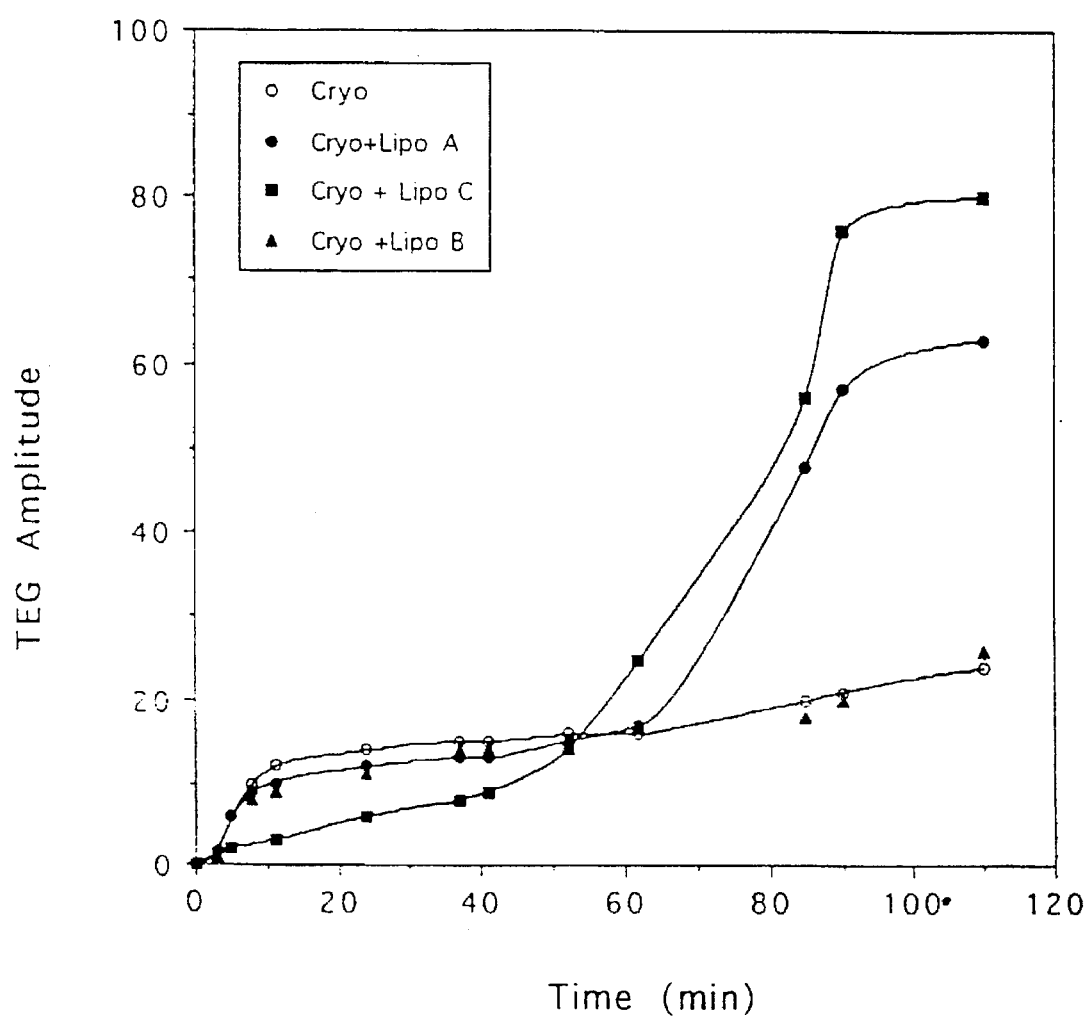
FIG. 5. Viscoelasticity development (expressed as thromboelastograph ("TEG") amplitude) of fibrin glue formulated with cryoprecipitate ("Cryo") and thrombin without (open circles) and with 5% (v/v) of neutral (Type A) liposomes ("Cryo+Lipo A", filled circles), amino (Type B) liposomes ("Cryo+Lipo B", filled triangles), and carboxylic acid (Type C) liposomes ("Cryo+Lipo C", filled squares).

For example, with low levels of thrombin (e.g. 0.5 U/mL final) mixed with fibrinogen from cryoprecipitate, Types A, B and C liposomes did not significantly increase the early phase of the development of viscoelasticity. However, after 60 minutes, Type A and Type C liposomes increased the final viscoelasticity of the fibrin glue, while Type B liposomes had no significant effect (FIG. 5). The results indicate that the amine groups on the surfaces of Type B liposomes may diminish the mechanical properties of the fibrin glue, probably by interfering with the cross-linking of fibrin instigated by factor XIIIa. At high levels of thrombin (e.g. >20 U/mL final), coagulation was essentially instantaneous, measurable TEG amplitude was maximized within 2 minutes, and no significant difference could be detected among any of the fibrin glue and liposome formulations. These results indicate that liposomes with different surface moieties, such as the amine or carboxylic acid groups of the Type B and Type C liposomes, respectively, can be formulated, as desired, to affect the mechanical properties of fibrin glue as desired or needed in using the bioadhesive liposome-containing fibrin glue compositions.

Figure 6:
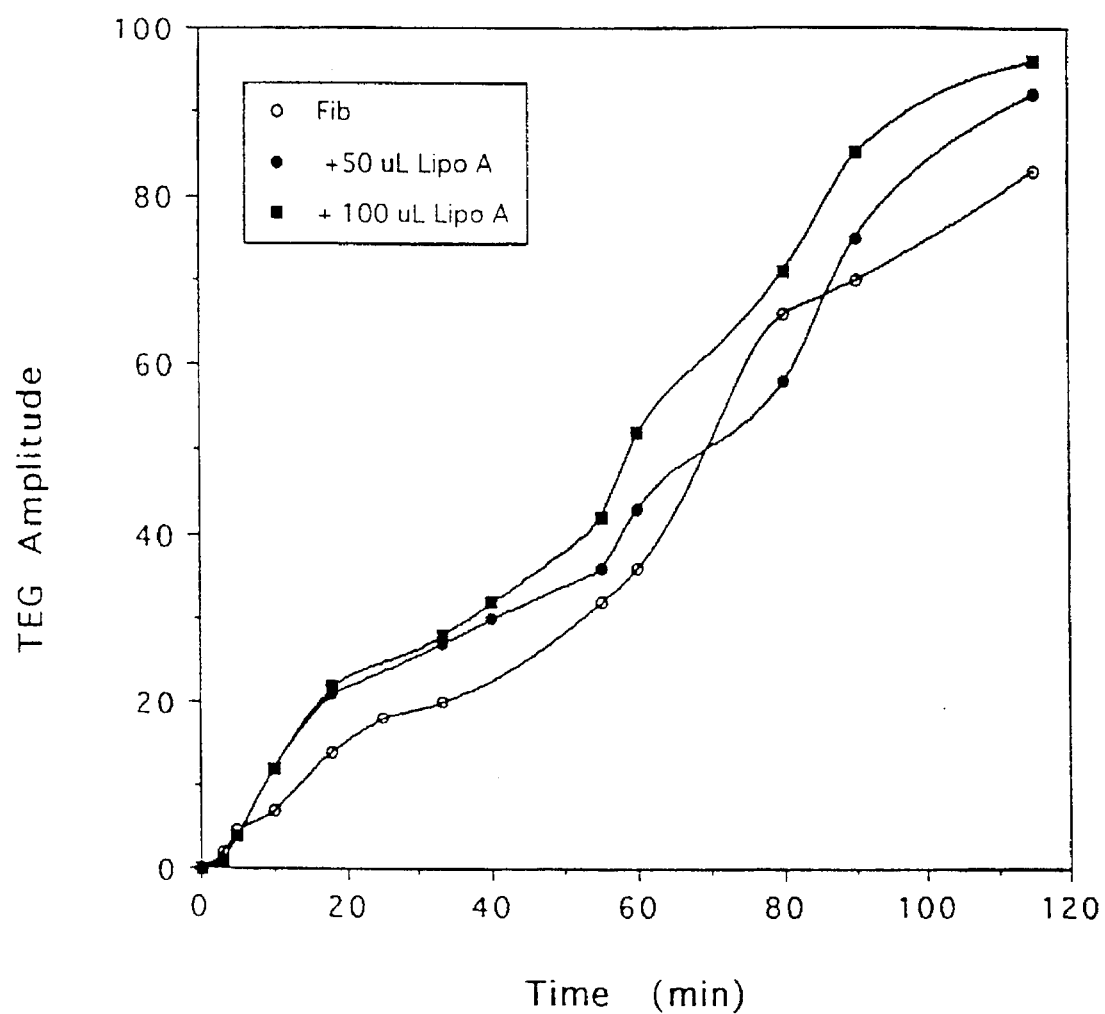
FIG. 6. Viscoelasticity development (expressed as thromboelastograph ("TEG") amplitude) of fibrin glue formulated with pure fibrinogen ("Fib", 3.6 mg/mL final concentration) and thrombin without (open circles) and with 50 µL (filled circles) or 100 µL (filled squares) of Type A liposomes ("Lipo A") added to the fibrin glue mixture (300 µL total).

In another series of experiments, the development of viscoelasticity was measured for pure fibrinogen, i.e. Cohn Fraction I purified fibrinogen, (final concentration: 3.6 mg/mL; final volume: 300 µL) mixed with different volumes (either 50 µL or 100 µL) of Type A liposome suspensions. Clotting (i.e., gelation) was initiated by low levels of thrombin (e.g. 0.5 U/mL). Here, a small but significant increase of the TEG amplitude was observed with added liposome volume (FIG. 6). These results indicate that fibrin glue may be formulated by altering the volume of liposomes added in a manner which does not significantly interfere with the viscoelastic properties of the final fibrin glue and liposome composition.

The ability of liposomes to modulate or not interfere with the viscoelastic properties of fibrin glue can be advantageous, such as when the fibrin glue and liposome composition is used to prepare films or membranes that need to remain flexible during use, or when the composition is used to coat the surface of a prosthetic device which itself flexes or changes shape during its intended use. Often, it is desired that such devices, coatings, or membranes be resident in vivo for long periods of time. However, normal lytic processes could degrade the fibrin glue rather rapidly. For such uses, liposomes could be prepared with proteolytic inhibitors encapsulated within their aqueous compartments. With the onset of degradation of the glue, liposomes would be exposed and slowly release their entrapped proteolytic inhibitors. This process would thereby decrease the rate of degradation of the fibrin glue and liposome film or membrane. Thus, liposomes would minimally affect and even augment the desired mechanical properties of fibrin glue and would ultimately increase the effective lifetime of the fibrin glue membrane, coating, or film.

EXAMPLE 10

In Vivo Animal Studies

Liposome and fibrin glue composition used in wound healing of skin incisions

To demonstrate the utility of liposomes entrapped in fibrin glue and used in animals, in vivo experiments were performed. For surgical incisions, a 2 cm longitudinal, full skin thickness, paraspinal incision was made on the dorsal region of adult (e.g., 6–8 week old) Sprague-Dawley mice. Fascia was cut away from the skin which was washed with physiological saline and dried with gauze to remove any blood from the field. The incision was either stapled or was sealed with fibrin glue without or with added liposomes which had been prepared to contain entrapped zinc as a type of bioadditive in accordance with the invention.

Essentially, the Type A liposomes (i.e., neutral) were prepared by injecting a warmed solution of cholesterol and lecithin into Tris-saline buffer, pH 7.4, which contained 2 mM Zn(II) salt, and the resulting liposomes were incubated and washed as described. A Zn(II) solution entrapped in liposomes was used as an exemplary bioadditive in the aqueous compartment of the liposome. One skilled in the art will appreciate that other bioadditives, and solutions containing such additives, are equally and particularly suitable for entrapment in the liposomes of the composition, as described in the Detailed Description of the Invention. The Zn(II)-loaded liposomes were analyzed by X-ray fluorescence and found to have encapsulated about 10–20% aqueous phase of their total volume. The Zn(II)-loaded liposomes were added to fibrinogen in cryoprecipitate (10% by volume) prior to mixing with thrombin at the site of incision, i.e., forming a fibrin glue and Zn(II)-loaded liposome matrix at the wound site.

The animals were allowed to heal and were sacrificed after 14 days. The skin incisions that had been sealed either with the fibrin glue and liposome-containing composition or with staples were excised and analyzed. The incision area was analyzed for the presence of zinc in the scar area utilizing the x-ray fluorescence technique exactly as described in the reference by Gorodetsky R., Sheskin J., and Weinreb, 1986, *Int. J. Determatol.* 25:440–445. In contrast to the control stapled wound that contained 6±2 ppm zinc as a normal background level, the wound tissue to which fibrin glue with zinc-entrapped liposomes had been applied, contained double the zinc level (i.e., 15±2 ppm). The level of zinc found at the site of the stapled wound and at the site of application of the fibrin glue and zinc-containing liposome composition was compared with the level of zinc normally present in a non-cut region of the animal's skin or tissue. The results showed that a significantly increased level of zinc was released from liposomes relative to that of the normal controls and of normal undamaged skin.

This experiment demonstrated that the liposomes delivered zinc (or other entrapped materials) to the tissue of an animal with a healing incision. These data showed that liposomes entrapped in fibrin glue delivered their encapsulated aqueous contents to a tissue site without interfering with the adhesion and sealing functions of the fibrin glue. Both the encapsulation of bioactive material in the liposomes and their fixation at a tissue site by fibrin glue were demonstrated to work in accordance with the invention as described.

EXAMPLE 11

Wounding and Tensile Strength of Fibrin Glue at Wound Site

Figure 7:
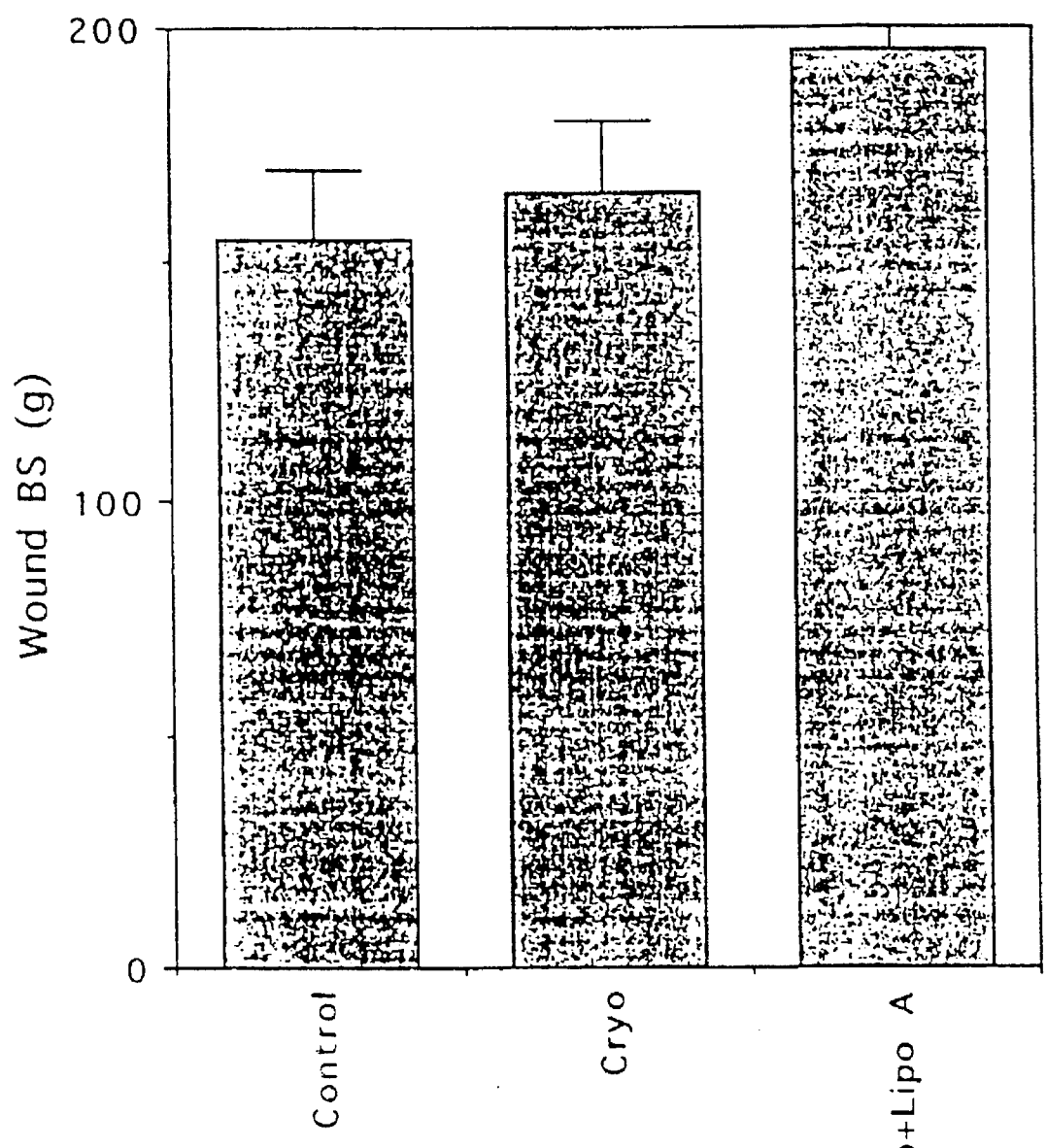
FIG. 7. Mean wound breaking strength ("Wound BS") of mouse skin incision closed with staples ("Control"), with fibrin glue formulated from cryoprecipitate ("Cryo") as a fibrinogen source, and with fibrin glue formulated from cryoprecipitate as a fibrinogen source in combination with Type A liposomes ("Cryo & Lipo A").

On the same tissue that was assayed for the presence of zinc, an analysis of the breaking strength of the healed wound incision was performed concomitantly. Mice (C3H strain) were shaved and a full depth incision (approximately 2 cm in length) was made dorsally. The wound cavity was sealed with fibrin glue: 1 mL fibrinogen (20 mg/ml) was placed in one syringe and 1 mL thrombin 0.5 U/ml, 2 mM Ca(II) and up to 200 µL liposomes were placed in a second syringe. The source of fibrinogen for preparation of the fibrin glue was from cryoprecipitate. As a control, fibrin glue was also formulated in the absence of liposomes and used to seal the incision. The contents of the syringes were released at the site of the incision to formulate the fibrin glue with or without added liposomes in situ. In other control animals, an incision was made as above, and the wound was closed with 4 surgical staples which were removed after 3 days. All of the mice were sacrificed after 3 days. A square of skin around the healed wound or control incision was excised immediately after sacrifice and was sliced perpendicular to the wound into 8 equivalent sections with a multiblade razor apparatus. The wound tensile strength (WTS) of the strips was measured in an Accuforce M 100 Tensile Strength Apparatus (Ametek), with the values expressed in grams per 2 mm wide strip. Each point generally represented the mean of about 28 to 42 measurements (e.g. 7 wound strips in 4 to 6 mice) with error bars representing the standard error of the mean (SEM). The WTS results obtained from control animals with stapled incisions, from control animals with wounds sealed with fibrin glue formulated without liposomes, and from experimental animals with wounds sealed with fibrin glue formulated with liposomes were compared (FIG. 7). These findings indicate that liposomes can augment the wound healing properties of fibrin glue.

EXAMPLE 12

Films or Membranes Produced by Fibrin Glue and Liposome Compositions

Figure 8:
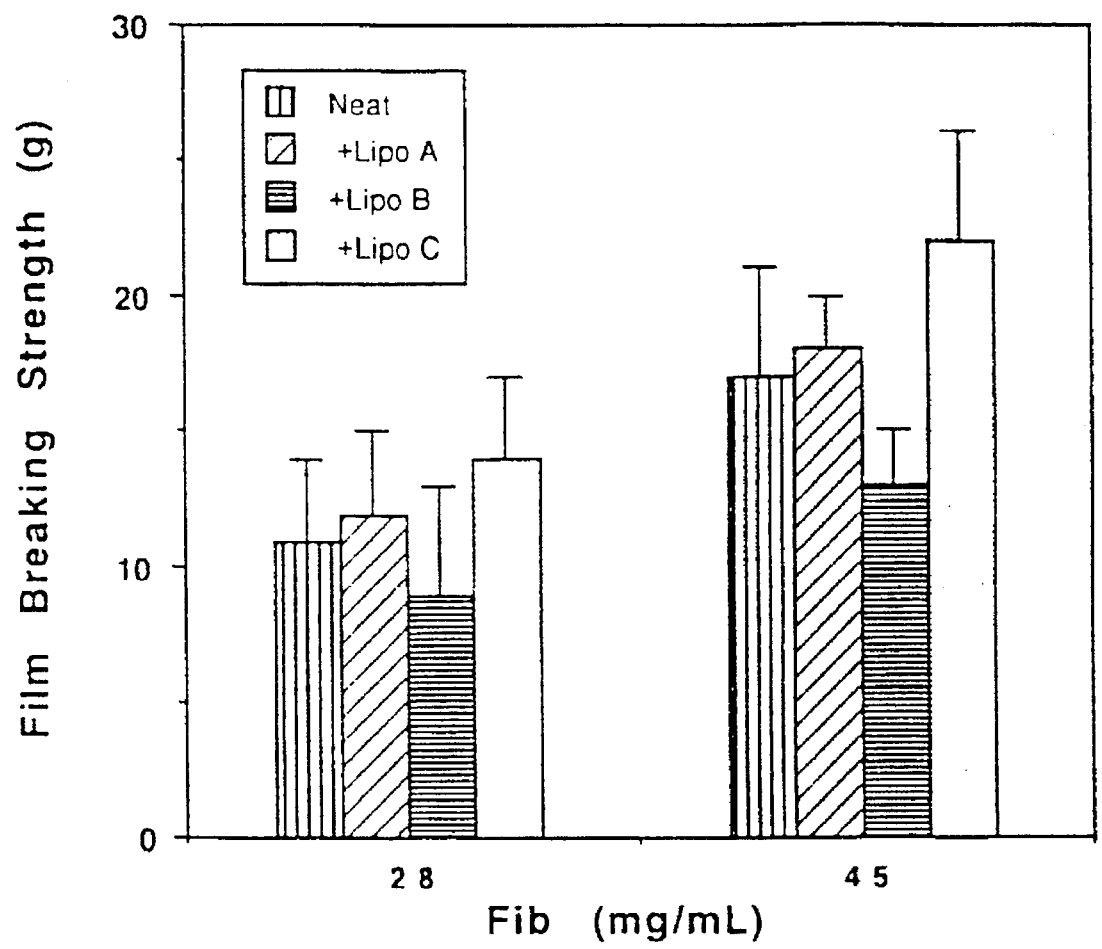
FIG. 8. Breaking strength (BS) of fibrin glue film without ("Neat") and with Type A, B, or C liposomes (8% by volume), ("Lipo A, Lipo B, Lipo C", respectively). Dimensions of fibrin glue film: 2 mm thick, 1 cm wide. Fibrin glue formulation: 28 mg/mL or 45 mg/mL fibrinogen ("Fib"); 10 U/mL thrombin; 15 mM Ca(II).
Figure 9:
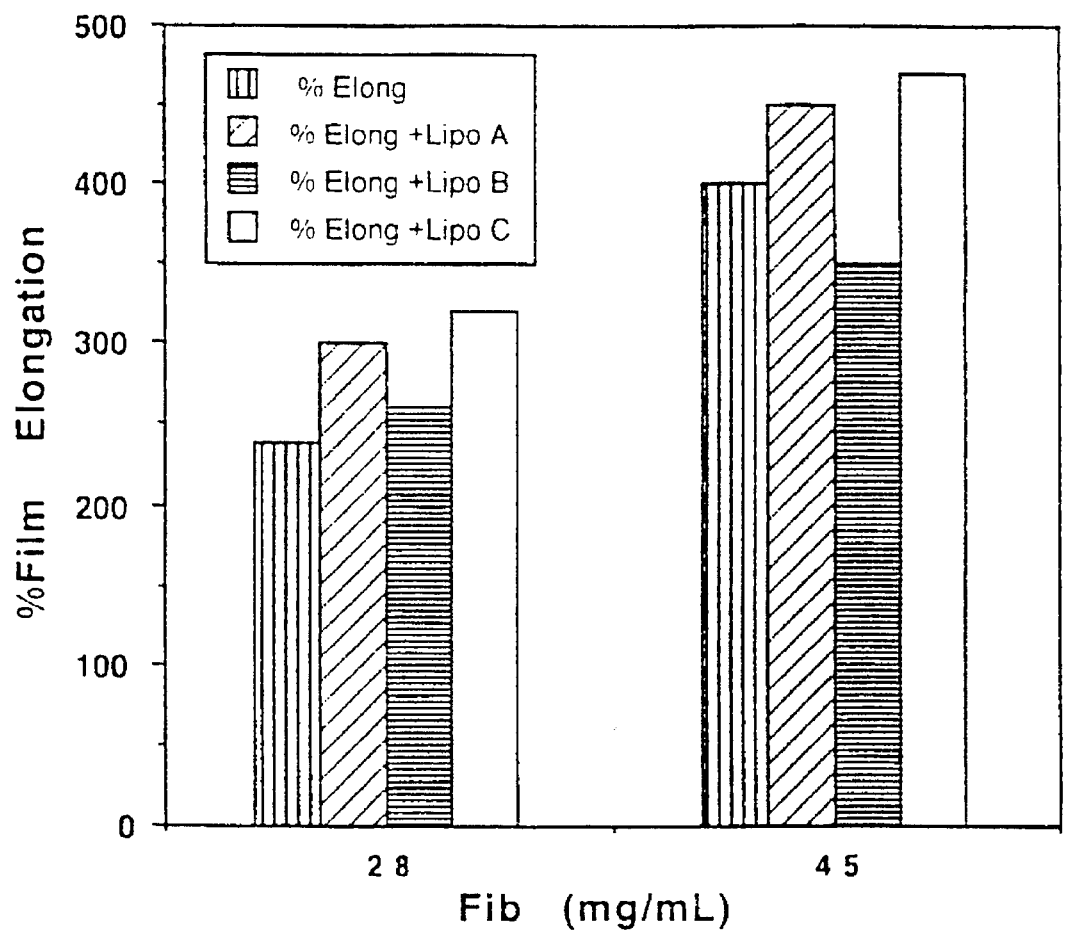
FIG. 9. Percent elongation ("% Elong") prior to breaking of fibrin glue film without and with Type A, B, or C liposomes (8% by volume), ("Lipo A, Lipo B, Lipo C", respectively). Initial dimensions: 2 mm thick, 1 cm wide. Fibrin glue formulation: 28 mg/mL or 45 mg/mL fibrinogen ("Fib"); 10 U/mL thrombin; 15 mM Ca(II).
Figure 11:
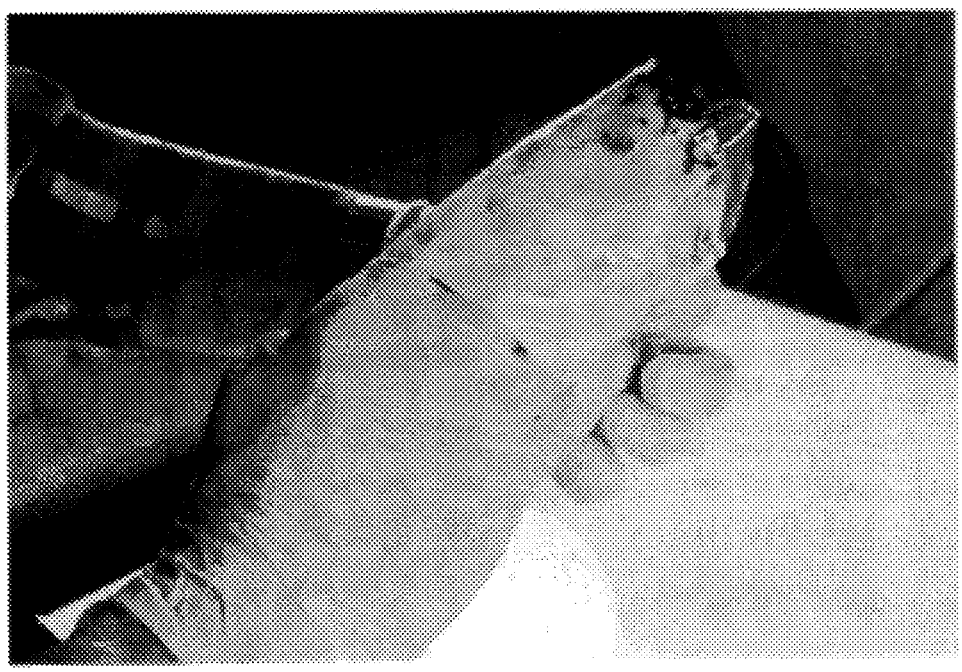
FIG. 11. Photograph of fibrin glue (45 mg/mL fibrinogen) containing Type A liposomes (8% by volume) flexibly coating aluminum foil as a solid substrate.

The addition of liposomes to fibrin glue can significantly and advantageously modify the physical characteristics of the film or membrane formed from the fibrin glue and liposome composition as described herein. For example, a 2 mm thick by 1 cm wide fibrin glue film made from fibrin glue containing 28 mg/mL fibrinogen, 10 U/mL thrombin, 15 mM Ca(II) solution, and liposomes (10% by volume) exhibited a breaking strength of 11 grams and became elongated by more than 200%. For convenience, the components used to formulate the fibrin glue and liposome composition were placed in an appropriate receptacle or container and sprayed onto the film or membrane; the spraying process mixed the components prior to their application to the substrate. After gelling or coagulation of the fibrin glue and liposome composition, the film or membrane of fibrin glue and liposomes was cleanly peeled away from the substrate film or membrane without the problems of sticking to the substrate or breakage during removal. For synthetic surfaces onto which the fibrin glue containing liposome film does adhere, the mechanism of adherence has not been completely elucidated, although ionic interactions are presumably involved. For films formulated with 45 mg/mL fibrinogen, 10 U/mL thrombin, and 15 mM Ca(II), an increase in film breaking strength is noted (e.g., to 18 g) (FIG. 8). In addition, Type A liposomes (i.e., neutral) and Type C liposomes (i.e., carboxylic acid) formulated in the fibrin glue composition increased the relative breaking strength and percent or degree of elongation, while Type B liposomes (i.e., amine) decreased the relative breaking strength and the percent of elongation before breaking (FIGS. 8 and 9). This example demonstrates that liposomes incorporated into fibrin glue films can modulate its physical parameters in a controlled manner, and also indicates that films to be used as wound dressings or membrane devices can be fabricated from fibrin glue films which contain liposomes.

EXAMPLE 13

Fibrin Glue and Liposome Composition for Sealing Bone Breaks

Figure 12:
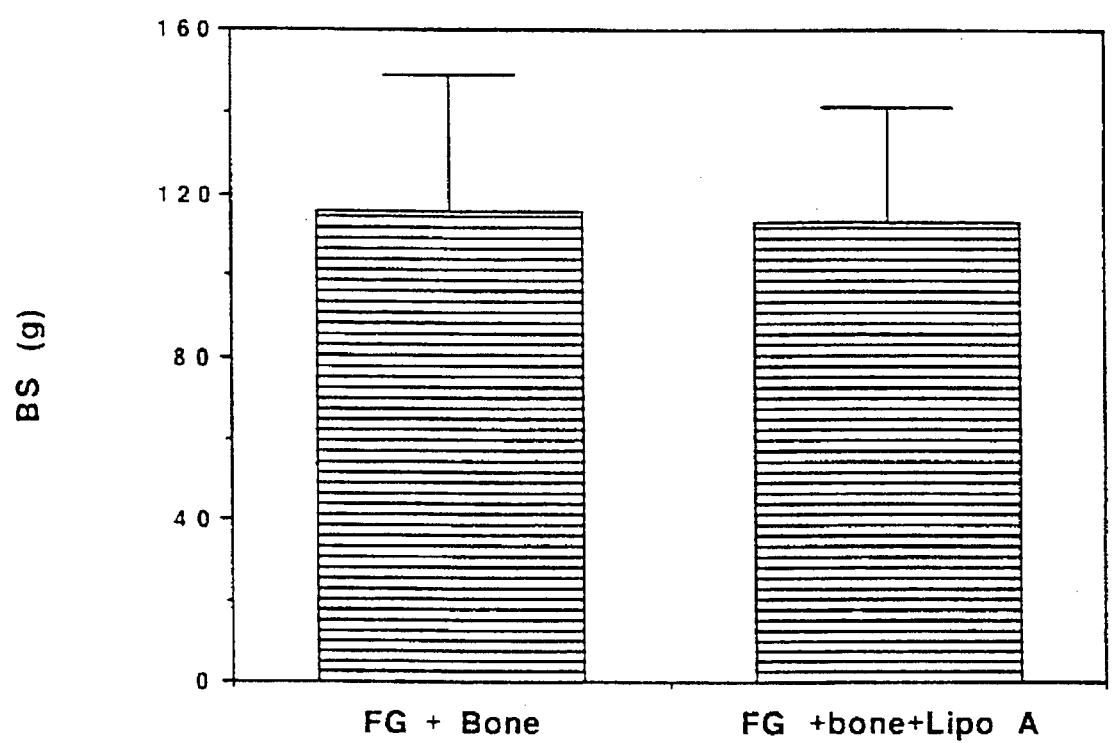
FIG. 12. Breaking strength (BS) of fibrin glue ("FG") mixed with bone fragments ("Bone") without or with Type A liposomes, 8% by volume, ("Lipo A"). Bone fragments not longer than 2 mM were mixed with fibrin glue without or with liposomes and the matrix was allowed to set for 1 hour at 37° C. in a moist environment. Fibrin glue components: fibrinogen (45 mg/mL), thrombin (2 U/mL), Ca(II) (15 mM).
Figure 12:
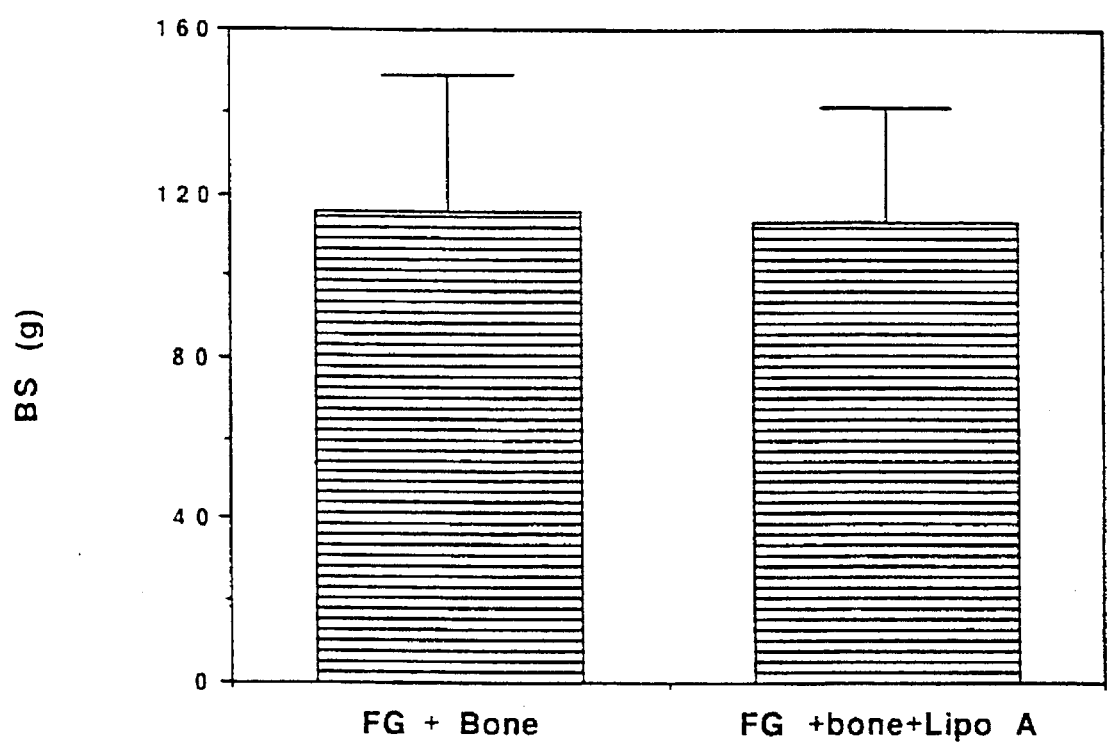

To illustrate the technique of using the fibrin glue containing liposome composition to seal and repair bone breaks, 50 mg of sheep femur bone fragments (not longer than 2 mM) were mixed with fibrin glue composed of 1 mL of 50 mg/mL fibrinogen without or with 5% (by volume) Type A liposomes, 300 µL of thrombin (10 U/mL), and 50 mM Ca(II). The fibrin glue, liposomes, and bone matrix was allowed to set for 1 hour and the breaking strength (BS) was measured using the techniques described above. The results indicated that Type A liposomes did not significantly decrease the mechanical properties of the fibrin glue and liposome composition which had been admixed with bone fragments (see FIG. 12).

The contents of the patents and references described and contained herein are incorporated by reference in their entirety.

Although the foregoing invention has been described in some detail by way of illustration and example for purposes of clarity of understanding, it will be obvious to those skilled in the art that certain changes and modifications may be practiced without departing from the spirit and scope thereof, as described in the specification and as defined in the appended claims.

What is claimed is:

1. A method for inducing coagulation of a liposome-containing fibrin glue bioadhesive composition at a site of injury, wound, or surgery in a mammal, thereby resulting in sealing and healing of the injury, wound, or surgical site, comprising:
   a) preparing said liposome-containing fibrin glue composition, comprising in admixture:
      (i) virus-inactivated fibrinogen present in said composition at a concentration of 10 to 90 mg/mL;
      (ii) virus-inactivated thrombin present in said composition at a concentration of 1 to 200 U/mL;
      (iii) liposomes present in said composition at a concentration of about 1% to 20%, by volume; and
      (iv) calcium present in said composition at a concentration of about 1 to 30 mM; and
   b) administering said composition to said mammal, wherein coagulation of said glue forms a medium for entrapping said liposomes at said site and embeds said liposomes in said glue.

2. The method according to claim 1, wherein said liposomes contain one or more medicaments within their interior aqueous phases.

3. The method according to claim 1, wherein said administering step is topical application.

4. A process for forming a flexible fibrin glue and liposome composition in the form of a film or membrane comprised of said fibrin glue in which said liposomes are embedded, the film or membrane used for coating or implantation in vitro or in vivo, comprising:
   a) preparing said fibrin glue and liposome composition comprising:
      i) virus-inactivated fibrinogen at a concentration of about 10 to 90 mg/mL;
      ii) virus-inactivated thrombin at a concentration of about 1 to 200 U/mL; and
      iii) liposomes at a concentration of about 1% to 20%, by volume;
   b) mixing the components of step a);
   c) sprayably applying the composition onto a substrate; the substrate providing a surface onto which the composition temporarily adheres and gels to form a flexible film or membrane comprising the gelled fibrin glue and liposome composition;
   d) removing from the substrate surface the film or membrane comprising the fibrin glue and liposome composition after said composition has gelled.

5. The process according to claim 4, wherein the liposomes are formulated to contain one or more medicaments within their interior aqueous phases.

6. A method for hemostatically sealing and healing a wound or a surgical incision and delivering to the wound or incision medicaments, comprising:
   a) preparing a liposome-containing fibrin glue composition, comprising in admixture:
      (i) virus-inactivated fibrinogen present in said composition at a concentration of 10 to 90 mg/mL;
      (ii) virus-inactivated thrombin present in said composition at a concentration of 1 to 200 U/mL;
      (iii) liposomes present in said composition at a concentration of about 1% to 20%, by volume, said liposomes formulated to contain one or more medicaments within their interior aqueous phases; and
      (iv) calcium present in said composition at a concentration of about 1 to 30 mM;
   b) administering said composition to the surface of said wound or incision, wherein coagulation of said glue forms a medium for entrapping said liposomes at said site, embeds said liposomes in said glue, and allows sustained release of said liposome contents delivered within said wound or incision.

7. The method according to claim 6, wherein said administering step is topical application.

8. The method according to claim 7, wherein said topical application comprises spraying or spreading.

9. The method according to claim 3, wherein said topical application comprises spraying or spreading.

10. The method according to claim 2 or claim 6, wherein said medicament contained within said liposomes is selected from the group consisting of neuroleptics, vitamins, growth factors, steroids, antibiotics, antibacterial compounds, bacteriocidal compounds, bacteriostatic compounds, antiviral compounds, antifungal compounds, antiparasitic compounds, tumoricidal compounds, tumoristatic compounds, toxins, enzymes, enzyme inhibitors, proteins, peptides, minerals, neurotransmitters, lipoproteins, glycoproteins, immunomodulators, immunoglobulins, dyes, radiolabels, radiopaque compounds, fluorescent compounds, fatty acids, polysaccharides, cell receptor binding molecules, anti-inflammatories, antiglaucomic compounds, mydriatic compounds, anesthetics, nucleic acids, and polynucleotides.

11. The process according to claim 5, wherein said medicament contained within said liposomes is selected from the group consisting of neuroleptics, vitamins, growth factors, steroids, antibiotics, antibacterial compounds, bacteriocidal compounds, bacteriostatic compounds, antiviral compounds, antifungal compounds, and parasitic compounds, tumoricidal compounds, tumoristatic compounds, toxins, enzymes, enzyme inhibitors, proteins, peptides, minerals, neurotransmitters, lipoproteins, glycoproteins, immunomodulators, immunoglobulins, dyes, radiolabels, radiopaque compounds, fluorescent compounds, fatty acids, polysaccharides, cell receptor binding molecules, anti-inflammatories, antiglaucomic compounds, mydriatic compounds, anesthetics, nucleic acids, and polynucleotides.

12. The method according to claim 1 or claim 6, wherein said fibrinogen is mixed with other proteins selected from the group consisting of proteins in uncoagulated whole blood and proteins in plasma and platelet-rich plasma.

13. The process according to claim 4, wherein said fibrinogen is mixed with other proteins selected from the group consisting of proteins in uncoagulated whole blood and proteins in plasma and platelet-rich plasma.

14. The composition according to claim 12, wherein said blood and plasma proteins are selected from the group consisting of fibrinogen, factor XIII, fibronectin, thrombin, immunoglobulin, plasminogen, and albumin.

15. The composition according to claim 13, wherein said blood and plasma proteins are selected from the group consisting of fibrinogen, factor XIII, fibronectin, thrombin, immunoglobulin, plasminogen, and albumin.

16. The method according to claim 1 or claim 6, wherein said liposomes are selected from the group consisting of liposomes formulated to contain noncharged chemical groups exposed on the liposome surface, thereby resulting in neutral liposomes; liposomes formulated to contain amine groups exposed on the liposome surface, thereby resulting in amine liposomes; and liposomes formulated to contain carboxylic acid groups exposed on the liposome surface, thereby resulting in carboxylic acid liposomes, or a mixture thereof.

17. The process according to claim 4, wherein said liposomes are selected from the group consisting of liposomes formulated to contain noncharged chemical groups exposed on the liposome surface, thereby resulting in neutral liposomes; liposomes formulated to contain amine groups exposed on the liposome surface, thereby resulting in amine liposomes; and liposomes formulated to contain carboxylic acid groups exposed on the liposome surface, thereby resulting in carboxylic acid liposomes, or a mixture thereof.

18. The method according to claim 2 or claim 6, wherein one medicament is contained within the aqueous compartment of a first set of liposomes selected from the group consisting of liposomes formulated to contain noncharged chemical groups exposed on the liposome surface, thereby resulting in neutral liposomes; liposomes formulated to contain amine groups exposed on the liposome surface, thereby resulting in mine liposomes; and liposomes formulated to contain carboxylic acid groups exposed on the liposome surface, thereby resulting in carboxylic acid liposomes, or a mixture thereof, and another medicament is contained within the aqueous compartment of a second set of liposomes selected from the group consisting of liposomes formulated to contain noncharged chemical groups exposed on the liposome surface, thereby resulting in neutral liposomes; liposomes formulated to contain amine groups exposed on the liposome surface, thereby resulting in amine liposomes; and liposomes formulated to contain carboxylic acid groups exposed on the liposome surface, thereby resulting in carboxylic acid liposomes, or a mixture thereof, said first and second sets of liposomes being mixed and sequestered in said fibrin glue from which the medicaments are released.

19. The process according to claim 5, wherein one medicament is contained within the aqueous compartment of a first set of liposomes selected from the group consisting of liposomes formulated to contain noncharged chemical groups exposed on the liposome surface, thereby resulting in neutral liposomes; liposomes formulated to contain amine groups exposed on the liposome surface, thereby resulting in amine liposomes; and liposomes formulated to contain carboxylic acid groups exposed on the liposome surface, thereby resulting in carboxylic acid liposomes, or a mixture thereof, and another medicament is contained within the aqueous compartment of a second set of liposomes selected from the group consisting of liposomes formulated to contain noncharged chemical groups exposed on the liposome surface, thereby resulting in neutral liposomes; liposomes formulated to contain amine groups exposed on the liposome surface, thereby resulting in amine liposomes; and liposomes formulated to contain carboxylic acid groups exposed on the liposome surface, thereby resulting in carboxylic acid liposomes, or a mixture thereof, said first and second sets of liposomes being mixed and sequestered in said fibrin glue from which the medicaments are released.

20. The method according to claim 16, wherein said noncharged or neutral lipids are lecithin or phosphatidylcholine.

21. The process according to claim 17, wherein said noncharged or neutral lipids are lecithin or phosphatidylcholine.

22. The method according to claim 16, wherein said amine is stearyl amine or diethylstearylamine.

23. The process according to claim 17, wherein said amine is stearyl amine or diethylstearylamine.

24. The method according to claim 16, wherein said carboxylic acid is stearic acid.

25. The process according to claim 17, wherein said carboxylic acid is stearic acid.

26. The method according to claim 1 or claim 6, wherein said liposomes are formulated to contain on their surfaces compounds having at least one light sensitive chemical double bond, said double bond predisposing the compounds to undergo conformational change when exposed to light, thereby resulting in photoactivable or light sensitive liposomes.

27. The method according to claim 26, wherein said double chemical bond-containing photoactivable compounds are selected from the group consisting of lecithins of retinoic acid and α-tocopherol.

28. The method according to claim 27, wherein said lecithins of retinoic acid are 1,2, diretinoyl-sn-3-glycerophosphocholine, 2-retinoylsolecithin, or 1-palmitoyl-2-retinoyl-sn-3-glycerophosphocholine.

29. The process according to claim 4, wherein said liposomes are formulated to contain on their surfaces compounds having at least one light sensitive chemical double bond, said double bond predisposing the compounds to undergo conformational change when exposed to light, thereby resulting in photoactivable or light sensitive liposomes.

30. The method according to claim 29, wherein said double chemical bond-containing photoactivable compounds are selected from the group consisting of lecithins of retinoic acid and α-tocopherol.

31. The method according to claim 30, wherein said lecithins of retinoic acid are 1,2, diretinoyl-sn-3-glycerophosphocholine, 2-retinoylisolecithin, or 1-palmitoyl-2-retinoyl-sn-3-glycerophosphocholine.

32. The method according to claim 1, wherein said fibrinogen is purified human fibrinogen and said thrombin is purified human or bovine thrombin.

33. The method according to claim 6, wherein said fibrinogen is purified human fibrinogen and said thrombin is purified human or bovine thrombin.

34. The process according to claim 4, wherein said fibrinogen is purified human fibrinogen and said thrombin is purified human or bovine thrombin.

* * * * *